United States Patent
Fang et al.

(10) Patent No.: US 8,658,353 B2
(45) Date of Patent: Feb. 25, 2014

(54) LIVER CELL TOXICITY ASSAY

(75) Inventors: Ye Fang, Painted Post, NY (US); Ann M. Ferrie, Painted Post, NY (US); Haiyan Sun, Baltimore, MD (US); Elizabeth Tran, Painted Post, NY (US); Ying Wei, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 933 days.

(21) Appl. No.: 12/613,966

(22) Filed: Nov. 6, 2009

(65) Prior Publication Data

US 2010/0129854 A1 May 27, 2010

Related U.S. Application Data

(60) Provisional application No. 61/117,838, filed on Nov. 25, 2008.

(51) Int. Cl.
*C12Q 1/70* (2006.01)

(52) U.S. Cl.
USPC .................................. 435/5; 435/6.1; 435/29

(58) Field of Classification Search
USPC .............................. 435/5, 6.1, 29; 702/19, 20
See application file for complete search history.

(56) References Cited

U.S. PATENT DOCUMENTS

2006/0223058 A1* 10/2006 Cox et al. .......................... 435/5

FOREIGN PATENT DOCUMENTS

| WO | WO 2005/008242 | 1/2005 |
| WO | WO 2006/108183 | 10/2006 |
| WO | WO 2008/060382 | 5/2008 |
| WO | WO 2009/002565 | 12/2008 |
| WO | WO 2009/111020 | 9/2009 |

OTHER PUBLICATIONS

Gomez-Lechon et al. "Long-term expression of differentiated functions in hepatocytes cultured in three-dimentional collagen matrix", J of Cellular Physiology, 1998, 177:553-562.*
Waring et al. "Clustering of hepatotoxins based on mechanism of toxicity using gene expression profiles", Toxicology and Applied Pharmacology, 2001, 175:28-42.*
Moghe et al. "Culture matrix configuration and composition in the maintenance of hepatocyte polarity and function", Biomaterials, 1996, vol. 17(3):373-385.*
Tsang et al. "Fabrication of 3D hepatic tissues by additive photopatterning of cellular hydrogels", The FASEB Journal, 2007, 21: 790-801.*
Y. Fang, et al., "Resonant Waveguide Grating Biosensor for Living Cell Sensing" Biophysical Journal, vol. 91, Sep. 2006, p. 1925-1940.
Y. Fang, et al., Characteristics of Dynamic Mass Redistribution of Epidermal Growth Factor Receptor Signaling in Living Cells Measured with Label-Free Optical Biosensors, Analytical Chemistry, vol. 77, 2005, pp. 5720-5725.
Y. Fang, et al., "Label-Free Cell-Based Assays with Optical Biosensors in Drug Discovery", Assays and Drug Development Technologies, vol. 4, No. 5, 2006, pp. 583-595.
S.N. Bhatia, et al., "Effect of Cell-Cell Interactions in Preservation of Cellular Phenotype: Cocultivation of Hepatocytes and Nonparenchymal Cells", The FASEB Journal, vol. 13, Nov. 1999, pp. 1883-1900.
N. Treijtel, et al., "The Use of Sandwich Cultured Rat Hepatocytes to Determine the Intrinsic Clearance of Compounds with Different Extraction Ratios 7-Ethoxycoumarin and Warfarin", Drug Metabolism and Disposition, vol. 33, No. 9, 2005, pp. 1325-1332.

* cited by examiner

*Primary Examiner* — Bin Shen
(74) *Attorney, Agent, or Firm* — John L. Haack

(57) ABSTRACT

The disclosure provides methods for characterizing the toxicity of a candidate molecule to liver cells as defined herein; methods of culturing metabolically active liver cells on a biosensor as defined herein; and biosensor liver culture systems as defined herein.

17 Claims, 7 Drawing Sheets a b

Time (sec)

a b

LIVER CELL TOXICITY ASSAY

CLAIMING BENEFIT OF PRIOR FILED U.S. APPLICATION

This application claims the benefit of U.S. Provisional Application Ser. No. 61/117,838, filed on Nov. 25, 2008. The content of this document and the entire disclosure of publications, patents, and patent documents mentioned herein are incorporated by reference.

The entire disclosure of any publication, patent, or patent document mentioned herein is incorporated by reference.

BACKGROUND

The disclosure relates to the field of biosensors, such as resonant waveguide grating (RWG) biosensors or surface plasmon resonance (SPR) biosensors or electric biosensors, and more specifically to methods of screening for molecule toxicity using a label-free liver cell assay. The disclosure also relates to a biosensor liver cell culture system and method of culturing liver cells.

SUMMARY

The disclosure provides methods for directly or indirectly characterizing the toxicity of molecules using a label-free liver cell assay. The disclosure also provides a biosensor liver culture system and method of culturing liver cells so as to present the liver cells to a biosensor surface while restoring or maintaining the metabolic and transporter functions of liver cells.

DETAILED DESCRIPTION

Figure 1:
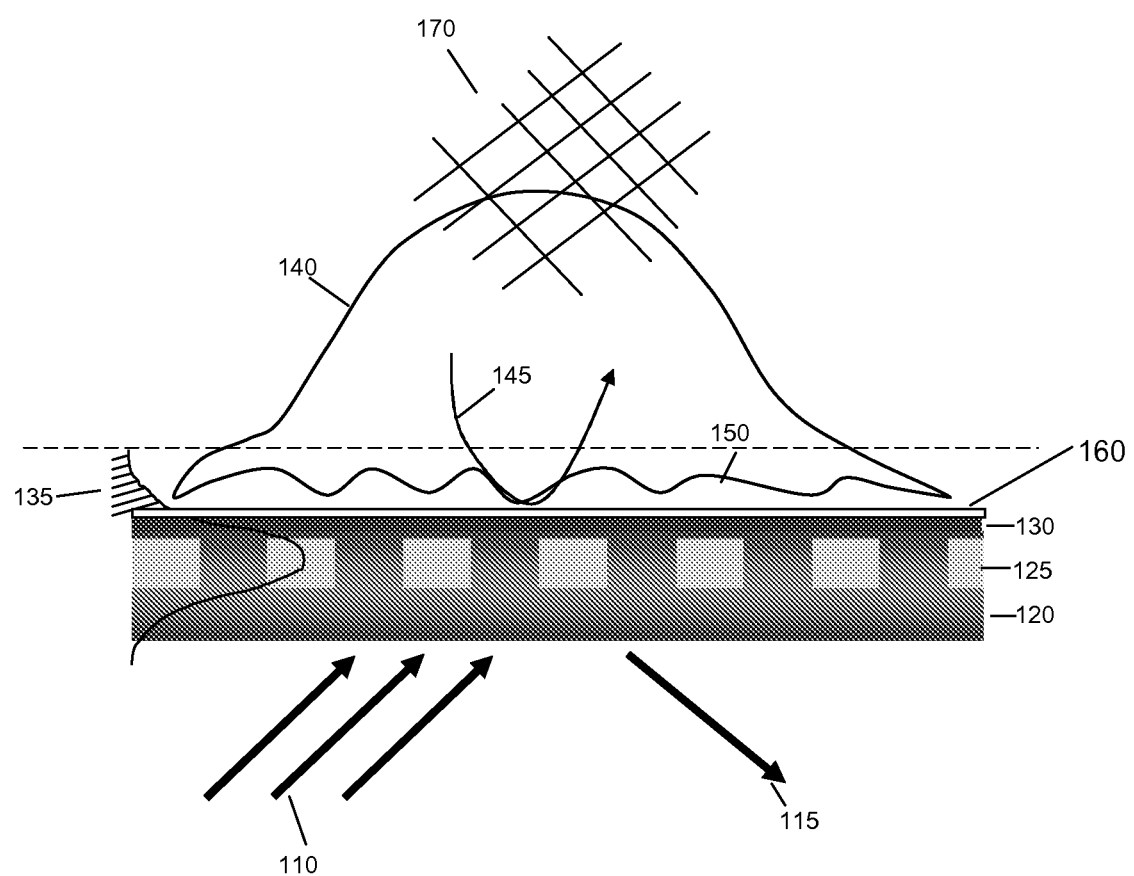
FIG. 1 shows a side view schematic of a biosensor liver cell culture system for detecting biosensor signal such as dynamic mass redistribution or dynamic cellular matter redistribution signal in liver cells, in embodiments of the disclosure.

Various embodiments of the disclosure will be described in detail with reference to drawings, if any. Reference to various embodiments does not limit the scope of the disclosure, which is limited only by the scope of the claims attached hereto. Additionally, any examples set forth in this specification are not intended to be limiting and merely set forth some of the many possible embodiments for the claimed invention.

A. Definitions

1. Molecule

As used herein, the terms "molecule" or like terms refers to a biological or biochemical or chemical entity that exists in the form of a chemical molecule or molecules with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecules, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word molecule would include the specific molecule and salts thereof, such as pharmaceutically acceptable salts.

2. Ligand

A ligand or like terms is a substance or composition or a molecule that is able to bind to and form a complex with a biomolecule to serve a biological purpose. Actual irreversible covalent binding between a ligand and its target molecule is rare in biological systems. Ligand binding to receptors alters the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters. Radioligands are radioisotope labeled ligands, while fluorescent ligands are fluorescently tagged ligands; both are used as tracers for receptor biology and biochemistry studies. Ligand and modulator are used interchangeably.

3. Molecule Mixture

A molecule mixture or like terms is a mixture containing at least two molecules. The two molecules can be, but not limited to, structurally different (i.e., enantiomers), or compositionally different (e.g., protein isoforms, glycoform, or an antibody with different poly(ethylene glycol) (PEG) modifications, or structurally and compositionally different (e.g., unpurified natural extracts, or unpurified synthetic compounds). According to certain embodiments of the disclosure, a molecule mixture can be treated as a molecule.

4. Test Molecule

A test molecule or like terms is a molecule which is used in a method to gain some information about the test molecule. A test molecule can be an unknown or a known molecule.

5. Drug Candidate Molecule

A drug candidate molecule or like terms is a test molecule which is being tested for its ability to function as a drug or a pharmacophore. This molecule may be considered as a lead molecule.

6. Modulate

To modulate, or forms thereof, means increasing, decreasing, or maintaining a cellular activity mediated through a cellular target. It is understood that wherever one of these words is used it is also disclosed that it could be, for example, 1%, 5%, 10%, 20%, 50%, 100%, 500%, or 1000% increased from a control, or it could be, for example, 1%, 5%, 10%, 20%, 50%, or 100% decreased from a control.

7. Cell

Cell or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

A cell can include different cell types, such as a cell associated with a specific disease, a type of cell from a specific origin, a type of cell associated with a specific target, or a type of cell associated with a specific physiological function. A cell can also be a native cell, an engineered cell, a transformed cell, an immortalized cell, a primary cell, an embryonic stem cell, an adult stem cell, a cancer stem cell, or a stem cell derived cell.

Human consists of about 210 known distinct cell types. The numbers of types of cells can almost unlimited, considering how the cells are prepared (e.g., engineered, transformed, immortalized, or freshly isolated from a human body) and where the cells are obtained (e.g., human bodies of different ages or different disease stages, etc).

8. Detect

"Detect" or like terms refer to an ability of the apparatus and methods of the disclosure to discover or sense a stimulus-induced cellular response and to distinguish the sensed responses for distinct stimuli.

9. Stimulus

"Stimulus," "therapeutic candidate molecule," "therapeutic candidate," "prophylactic candidate," "prophylactic agent," "ligand candidate," "candidate molecule," or like terms refer to a molecule or material, naturally occurring or synthetic, which is of interest for its potential to interact with a cell attached to the biosensor. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid or like structure or component of a living cell.

10. Extracellular Matrix Material

"Extracellular matrix material" or like terms refer to biological material found in tissue and outside of cells that is able to provide structural support to cells. The extracellular matrix material can be a protein, a polysaccharide, or a glycoprotein. In embodiments, the extracellular matrix material can be, for example, a collagen (e.g., collagen I or collagen IV), laminin, gelatin, fibronectin, matrigel, or combinations thereof.

11. Amplifying Marker

"Amplifying marker," "marker," or like terms refer to any compound that can be used to indirectly determine toxicity or protectiveness. The amplifying marker can be any agent that can be used to probe toxicity or protectiveness. The amplifying marker also can be any agent that can be used to amplify toxicity or protectiveness. Specifically, for liver cell toxicity, the amplifying marker can be any agent to which a cell can become susceptible as a result of exposure to a candidate molecule. The amplifying marker also can be any agent that a cell can become resistant to as a result of exposure to a candidate molecule. The amplifying marker also can be any agent that exhibits synergistic effects with a candidate molecule. Such amplifying markers include, for example, hydrogen peroxide, hepatotoxins, carbonyl cyanide m-chlorophenyl hydrazone, ethanol, and dimethyl sulfoxide (DMSO).

12. Overlay

"Overlay" or like terms refer to an immobilized composite structure comprising liver cells and an extracellular matrix material. The overlay matrix material can support the liver cells with the composite structure. The overlay matrix material also can cover the liver cells. The overlay can take place by adding an ECM to a solution covering a liver cell, such that the ECM binds to cell surface receptors.

13. Metabolic Function

"Metabolic function" or like terms refer to the ability of a cell, tissue, organ, or organism to breakdown chemical compounds into metabolites.

14. Portion

"A portion" or like terms refer to a value in the range of about 10% to about 90% of the full amount. The portion can be about 10%, about 20%, about 30%, about 40%, about 50%, about 60%, about 70%, about 80%, or about 90% of the full amount.

15. Include

"Include," "includes," or like terms means including but not limited to.

16. Cell Culture

"Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues and organs.

17. Biosensor

Biosensor or like terms refer to a device for the detection of an analyte that combines a biological component with a physicochemical detector component. The biosensor typically consists of three parts: a biological component or element (such as tissue, microorganism, pathogen, cells, or combinations thereof), a detector element (works in a physicochemical way such as optical, piezoelectric, electrochemical, thermometric, or magnetic), and a transducer associated with both components. The biological component or element can be, for example, a living cell, a pathogen, or combinations thereof. In embodiments, an optical biosensor can comprise an optical transducer for converting a molecular recognition or molecular stimulation event in a living cell, a pathogen, or combinations thereof into a quantifiable signal.

18. Assaying

Assaying, assay, or like terms refers to an analysis to determine a characteristic of a substance, such as a molecule or a cell, such as for example, the presence, absence, quantity, extent, kinetics, dynamics, or type of an a cell's optical or bioimpedance response upon stimulation with one or more exogenous stimuli, such as a ligand or marker. Producing a biosensor signal of a cell's response to a stimulus can be an assay. For example, producing a DMR profile of a cell's response to a stimulus using an optical biosensor can be an assay.

19. Treating

Treating or treatment or like terms can be used in at least two ways. First, treating or treatment or like terms can refer to administration or action taken towards a subject. Second, treating or treatment or like terms can refer to mixing any two things together, such as any two or more substances together, such as a molecule and a cell. This mixing will bring the at least two substances together such that a contact between them can take place.

When treating or treatment or like terms is used in the context of a subject with a disease, it does not imply a cure or even a reduction of a symptom for example. When the term therapeutic or like terms is used in conjunction with treating or treatment or like terms, it means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

20. Contacting

Contacting or like terms means bringing into proximity such that a molecular interaction can take place, if a molecular interaction is possible between at least two things, such as molecules, cells, markers, at least a compound or composition, or at least two compositions, or any of these with an article(s) or with a machine. For example, contacting refers to bringing at least two compositions, molecules, articles, or things into contact, i.e. such that they are in proximity to mix or touch. For example, having a solution of composition A and cultured cell B and pouring or adding solution of composition A over cultured cell B would be bringing solution of composition A in contact with cell culture B. Contacting a cell with a ligand would be bringing a ligand to the cell to ensure the cell have access to the ligand.

It is understood that anything disclosed herein can be brought into contact with anything else. For example, a cell can be brought into contact with a marker or a molecule, a biosensor, and so forth.

21. Trigger

A trigger or like terms refers to the act of setting off or initiating an event, such as a response.

22. Response

A response or like terms is any reaction to any stimulation.

23. Cellular Response

A "cellular response" or like terms is any reaction by the cell to a stimulation.

24. Biosensor Response

A "biosensor response", "biosensor output signal", "biosensor signal" or like terms is any reaction of a sensor system having a cell to a cellular response. A biosensor converts a cellular response to a quantifiable sensor response. A biosensor response is an optical response upon stimulation as measured by an optical biosensor such as RWG or SPR or it is a bioimpedence response of the cells upon stimulation as measured by an electric biosensor. Since a biosensor response is directly associated with the cellular response upon stimulation, the biosensor response and the cellular response can be used interchangeably, in embodiments of disclosure.

25. DMR Response

A "DMR response" or like terms is a biosensor response using an optical biosensor. The DMR refers to dynamic mass redistribution or dynamic cellular matter redistribution. A P-DMR is a positive DMR response, a N-DMR is a negative DMR response, and a RP-DMR is a recovery P-DMR response.

26. Assaying the Response

"Assaying the response" or like terms means using a means to characterize the response. For example, if a molecule is brought into contact with a cell, a biosensor can be used to assay the response of the cell upon exposure to the molecule.

27. A Profile

A profile or like terms refers to the data which is collected for a composition, such as a cell. A profile can be collected from a label free biosensor as described herein.

28. Primary Profile

A "primary profile" or like terms refers to a biosensor output signal or profile which is produced when a molecule contacts a cell. Typically, the primary profile is obtained after normalization of initial cellular response to the net-zero biosensor signal (i.e., baseline).

29. In the Presence of the Molecule

"in the presence of the molecule" or like terms refers to the contact or exposure of the cultured cell with the molecule. The contact or exposure can be taken place before, or at the time, the stimulus is brought to contact with the cell.

30. Biosensor Signal

A "biosensor signal" or like terms refers to the signal of cells measured with a biosensor that is produced by the response of a cell upon stimulation.

31. DMR Signal

A "DMR signal" or like terms refers to the signal of cells measured with an optical biosensor that is produced by the response of a cell upon stimulation.

32. Control

The terms control or "control levels" or "control cells" or like terms are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard. For example, a control can refer to the results from an experiment in which the subjects or objects or reagents etc are treated as in a parallel experiment except for omission of the procedure or agent or variable etc under test and which is used as a standard of comparison in judging experimental effects. Thus, the control can be used to determine the effects related to the procedure or agent or variable etc. For example, if the effect of a test molecule on a cell was in question, one could a) simply record the characteristics of the cell in the presence of the molecule, b) perform a and then also record the effects of adding a control molecule with a known activity or lack of activity, or a control composition (e.g., the assay buffer solution (the vehicle)), and then compare effects of the test molecule to the control molecule. In certain circumstances once a control is performed the control can be used as a standard, in which the control experiment does not have to be performed again and in other circumstances the control experiment should be run in parallel each time a comparison will be made.

33. Positive Control

A "positive control" or like terms is a control that shows that the conditions for data collection can lead to data collection.

34. Characterizing

Characterizing or like terms refers to gathering information about any property of a substance, such as a ligand, molecule, marker, or cell, such as obtaining a profile for the ligand, molecule, marker, or cell.

35. Potentiate

Potentiate, potentiated or like terms refers to an increase of a specific parameter of a biosensor response of a marker in a cell caused by a molecule. By comparing the primary profile of a marker with the secondary profile of the same marker in the same cell in the presence of a molecule, one can calculate the modulation of the marker-induced biosensor response of the cells by the molecule. A positive modulation means the molecule to cause increase in the biosensor signal induced by the marker.

36. Higher and Inhibit and Like Words

The terms higher, increases, elevates, or elevation or like terms or variants of these terms, refer to increases above basal levels, e.g., as compared a control. The terms low, lower, reduces, decreases or reduction or like terms or variation of these terms, refer to decreases below basal levels, e.g., as compared to a control. For example, basal levels are normal in vivo levels prior to, or in the absence of, or addition of an agent such as an agonist or antagonist to a cell. Inhibit or forms of inhibit or like terms refers to reducing or suppressing.

37. Cellular Target

A "cellular target" or like terms is a biopolymer such as a protein or nucleic acid whose activity can be modified by an external stimulus. Cellular targets are most commonly proteins such as enzymes, kinases, ion channels, and receptors.

38. Molecule-Treated Cell

A molecule-treated cell or like terms is a cell that has been exposed to a molecule.

39. Cellular Process

A cellular process or like terms is a process that takes place in or by a cell. Examples of cellular process include, but not limited to, proliferation, apoptosis, necrosis, differentiation, cell signal transduction, polarity change, migration, or transformation.

40. Attach

"Attach," "attachment," "adhere," "adhered," "adherent," "immobilized", or like terms generally refer to immobilizing or fixing, for example, a surface modifier substance, a compatibilizer, a cell, a ligand candidate molecule, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with cell anchoring materials, compatibilizer (e.g., fibronectin, collagen, lamin, gelatin, polylysine, etc.), or both.

41. Adherent Cells

"Adherent cells," "immobilized cells", or like terms refer to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues and organs.

42. Cell System

"Cell system" or like terms refers to a collection of more than one type of cells (or differentiated forms of a single type of cell), which interact with each other, thus performing a biological or physiological or pathophysiological function. Such cell system includes an organ, a tissue, a stem cell, a differentiated hepatocyte cell, or the like. For example, a liver cell system would mean that a cell system contains a hepatocyte cell and a non-hepatocyte cell.

43. Liver Cells

"Liver cells" or like terms refer to cells that are either derived from or obtained from liver tissue. Liver cells can include primary liver cells, transformed liver cells such as hepatocyte HepG2C3A, and immortalized liver cells such as F2N4 cells. In embodiments, the liver cells can include helper cells. Examples of suitable helper cells include fibroblasts such as NIH 3T3 fibroblasts, murine 3T3-J2 fibroblasts or human fibroblast cells; human or rat hepatic stellate cells; and Kupffer cells.

44. Subject

As used throughout, by a subject or like terms is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) and mammals, non-human mammals, primates, non-human primates, rodents, birds, reptiles, amphibians, fish, and any other animal. In one aspect, the subject is a mammal such as a primate or a human. The subject can be a non-human.

45. Optional

"Optional" or "optionally" or like terms means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

46. A

As used in the specification and the appended claims, the singular forms "a," "an" and "the" or like terms include plural referents unless the context clearly dictates otherwise. Thus, for example, reference to "a pharmaceutical carrier" includes mixtures of two or more such carriers, and the like.

47. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

48. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

49. Comprise

Throughout the description and claims of this specification, the word "comprise" and variations of the word, such as "comprising" and "comprises," means "including but not limited to," and is not intended to exclude, for example, other additives, components, integers or steps.

50. Consisting Essentially of

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, aberrant affinity of a stimulus for a cell surface receptor or for an intracellular receptor, anomalous or contrary cell activity in response to a ligand candidate or like stimulus, and like characteristics.

51. Stable

When used with respect to pharmaceutical compositions, the term "stable" or like terms is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

52. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these molecules may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

53. Or

The word "or" or like terms as used herein means any one member of a particular list and also includes any combination of members of that list.

54. Publications

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

55. Sample

By sample or like terms is meant an animal, a plant, a fungus, etc.; a natural product, a natural product extract, etc.; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

56. About

About modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

57. Values

Specific and preferred values disclosed for components, ingredients, additives, cell types, markers, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

58. Compounds and Compositions

Thus, the claimed invention can suitably comprise, consist of, or consist essentially of: a method for characterizing the toxicity of a candidate molecule to liver cells as defined herein; a method of culturing metabolically active liver cells on a biosensor as defined herein; or a biosensor liver culture system as defined herein.

Compounds and compositions have their standard meaning in the art. It is understood that wherever, a particular designation, such as a molecule, substance, marker, cell, or reagent compositions comprising, consisting of, and consisting essentially of these designations are disclosed. Thus, where the particular designation marker is used, it is understood that also disclosed would be compositions comprising that marker, consisting of that marker, or consisting essentially of that marker. Where appropriate wherever a particular designation is made, it is understood that the compound of that designation is also disclosed. For example, if particular biological material, such as epidermal growth factor (EGF), is disclosed EGF in its compound form is also disclosed.

B. Compositions, Methods, Articles, and Machines

Screening for compound molecule toxicity can present a bottleneck in the drug discovery process. New technologies have led to a dramatic increase in the number of compounds that have pharmacologic potential, but the slowness of toxicity screening prevents many compounds from ever being tested and therefore slows the process of drug discovery and bringing new drugs to market. Often, researchers must select drug candidates for studies based on limited information. Thus, there is a need for rapid, in vitro testing methods that can mimic human metabolism and test for cell-specific toxicity of these potential drugs and, just as importantly, their metabolites.

1. Liver

The liver is the primary site of detoxification of many toxic substances from the blood, as well as the synthesis and secretion of many compounds. The liver also is the primary site of metabolism of the vast number and types of chemicals that humans are exposed to on a daily basis. The most important class of metabolic enzymes in the liver is the cytochrome P450s, which are actively involved in the clearance of drugs. The P450s start the process of breaking down chemicals so they can be excreted. Metabolism in the liver can create active metabolites which have desired pharmacologic effects. Importantly, liver metabolism also can produce toxic metabolites, such as in the breakdown of the common analgesic acetaminophen.

Hepatocytes, the cells that make up 70-80% of the cytoplasmic mass of the liver, carry out most of the metabolic and biosynthetic processes in the liver. Thus, in vitro cultured hepatocytes can be utilized for drug metabolism and toxicity studies. Much of the screening for metabolism and toxicity is done in primary human hepatocytes (cells isolated from liver), or human liver surrogates including animal hepatocytes and whole animals. Toxicology studies performed in animals are occasionally misleading but, more importantly, are too slow to be used for real-time feedback in a drug discovery campaign. Optimal lead development requires that the pharmacological properties of the compound or molecule be maximized simultaneously with the therapeutic properties. Early hits need to be ranked and examined quickly so that the information can be used to guide new synthesis.

2. In Vitro Assays

In vitro cell-based assays can provide essential information about the potential effects of chemicals on specific cell properties, and can provide a more relevant and more manageable basis for molecular and mechanistic studies than the conventional laboratory animal models do. Most cell assays for liver cell toxicity determination utilize a specific singular readout, such as the expression of a metabolic enzyme (e.g., CYP), or a secreted protein from the liver cells. However, cells are finely balanced homeostatic machines that respond to external stimuli through complex pathways. Therefore, because toxicity could be the result of a multitude of cellular events, including changes in cell morphology, differentiation, proliferation, function, excitability and/or communication, such systems can be inadequate for risk assessment purposes. For example, cell culture systems often lack essential systemic contributors to overall absorption, distribution, metabolism and excretion (ADME), and the complex interactions and effects of the immune, endocrine and nervous systems.

By adding subcellular or cellular metabolizing systems and assessing the production of known metabolites, problems with metabolic competence can be circumvented. This is particularly important when considering the elimination of lipophilic compounds, which is crucially reliant on phase I metabolism that can generate toxic intermediates from innocuous parent chemicals. The most important enzymes involved in such metabolism are the cytochrome P450-mixed function monooxygenases (CYPs), which have wide substrate specificity, and vary in nature and activity according to tissue and species. Metabolic cellular systems can be divided into three main categories: (i) metabolically-competent indicator cells (e.g. hepatocytes); (ii) co-culture systems comprising non-competent indicator cells (e.g. fibroblasts) and metabolically-competent cells (e.g. hepatocytes); and (iii) genetically engineered cell lines that can simultaneously act as both indicators of selected metabolic pathways and of toxicity.

3. Genomic Screening

Genomic (or transcriptomic), proteomic and metabonomic approaches to screening for toxicity are based on the premise that physiological, pharmacological and toxicological events can change the protein compositions and activities of cells and, hence, their structural and functional characteristics. These technologies aim to transform traditional toxicology by providing a means of deciphering specific mechanisms of toxicity, and by providing biomarkers for individual variations in susceptibility to toxicants and for use as early indicators of toxic exposure and effect. This can be achieved, following exposure to a test compound, by comparing gene expression profiles at either the transcriptional (genomic) level or the translational (proteomic) level with expression profiles specific to exposure to known toxicants. Differential transcription can be measured by microanalysis, in which extracted RNA is subjected to reverse transcription to obtain labeled cDNA or to RNA polymerase amplification to generate labeled cRNA. These species are hybridized to microarrayed oligonucleotides, then scanned under laser light to record between hundreds and hundreds of thousands measurements of gene expression. The design of highly specific panels of oligonucleotides can permit dose-dependent and tissue-dependent temporal and spatial patterns to be monitored. Unfortunately, this approach remains highly reliant on transcriptomic information that is currently limited.

Proteomic approaches to screening for toxicity are based on the analysis of functionally, structurally or anatomically related proteins (protein clusters) to determine physiologically or pathologically significant patterns of protein expression. Such approaches are largely based on the 2D electrophoretic resolution of proteins according to size and charge, followed by proteolytic cleavage, peptide mass determination and peptide identification. Unfortunately, proteomics suffers from two important limitations: (i) the process of sub-fractionation of tissue or cell samples is complicated and prone to contamination problems, and (ii) protein expression patterns vary greatly between samples in response to circadian cycles, age, sex and disease.

The present drug discovery approaches and methods can use any of the method components disclosed herein including but not limited to modulating, cell culturing, assaying, long term assaying, short term assaying, two step assaying, pulse stimulation assaying, treating, contacting, triggering, detecting, assaying the response, normalizing, characterizing, potentiating, modulating the biosensor signal, modulating the DMR signal, and attaching.

It is understood that any of the components can be used in any combination herein, and each permutation is specifically recited herein, at least for the components recited in the above component lists.

4. Indirect Method for Characterizing Toxicity

Compound toxicity can occur at different levels, such as genomic, proteomic, metabolic pathway, cellular, or organism level. Ideally compound toxicity screening involves a suite of assays that include CYP inductions, P-gp inhibition, and multiple toxicity assays. Unfortunately, the complexity of compound toxicity can make it practically difficult to represent the overall toxicity of a compound on cells.

Label-free cell-based assays generally employ a biosensor to monitor compound or stimulus induced responses in living cells. These label-free cellular assays typically measure an integrated cellular response. For example, label-free optical biosensor cellular assays can measure ligand-induced dynamic mass redistribution (DMR) signals in living cells. The resultant DMR signal is a real time kinetic measurement of cellular response, including receptor signaling and compound-induced toxicity. The DMR signals can contain systems cell biology and systems cell pharmacology information, and can offer a global representation of drug, pharmacology and toxicity. Unfortunately, label-free biosensors, particularly evanescent wave-based optical biosensors, can have a small detection volume which can limit the directly detectable changes in cells to the bottom portion of cell layers cultured on the biosensor surfaces. This is a significant drawback for probing cellular activities, including compound-induced toxicity.

Thus, the disclosure provides methods for indirectly characterizing the toxicity of a candidate molecule to liver cells, such as primary liver cells, using, for example, a Corning® Epic® biosensor system, or other biosensor systems.

In embodiments the disclosure provides a method for indirectly characterizing the toxicity of a candidate molecule to liver cells, the method comprising: providing a biosensor comprising liver cells immobilized on the biosensor's surface; contacting the immobilized liver cells with a candidate molecule; contacting the candidate molecule contacted immobilized cells with an amplifying marker; and detecting and comparing the amplifying marker induced biosensor response of the liver cells in the presence and absence of the candidate molecule.

In embodiments the immobilized liver cells can be immobilized, for example, within a sandwich culture system between double layers of extra-cellular matrix (ECM), in which the substrate surfaces are coated with an ECM protein such as collagen I.

ECM coatings, such as collagen I, can be necessary to maintain primary hepatocyte viability in culture. However, the microscale topology of cell and ECM contacts can alter hepatocyte phenotype (Bhatia et al., 1999), indicating that methods for controlling cellular organization are important. Thus, in particular embodiments, the present invention uses liver cells immobilized between nanoscale or microscale clusters of a first extra cellular matrix material coated on the biosensor's surface and an overlay of a second extra cellular matrix material. The use of a biosensor surface having a coating of clusters of an ECM material can provide appropriate microscale or nanoscale ECM topology for desired hepatocyte phenotype, and also can enable robust detection of compound toxicity and liver cell functions with these label-free biosensor cellular assays. Thus, in embodiments, the immobilized liver cells retain at least a portion of their metabolic function.

In alternative embodiments, the biosensor surface can be coated with amine reactive polymers, in which the liver cells can be covalently coupled to the surface. The polymer surface can be further modified with cell resistant molecules (such as polyethylene glycol) such that the number of amine reactive sites on the surface is relatively low, and cells remain non-spreading state.

In embodiments the first and second extra cellular matrix materials comprise essentially any type of biological material found in tissue and outside of cells that is able to provide structural support to cells. The extracellular matrix material can be a protein, a polysaccharide, or a glycoprotein. In embodiments, the extracellular matrix material can be, for example, a collagen (e.g., collagen I or collagen IV), fibronectin, laminin, gelatin, Matrigel™, or a combination thereof. In particular embodiments, the first extra cellular matrix material comprises collagen I and the second extra cellular matrix material comprises Matrigel™.

In embodiments the liver cells comprise at least one of: a primary liver cell, a transformed liver cell, an immortalized liver cell, or a combination thereof.

In embodiments the amplifying marker comprises essentially any agent that a cell can become susceptible to or resistant to as a result of exposure to a candidate molecule. The marker can comprise, for example, at least one of: hydrogen peroxide, ethanol, carbonyl cyanide m-chlorophenyl hydrazone, dimethyl sulfoxide, or a combination thereof.

In embodiments, the detected biosensor response comprises the dynamic mass redistribution of the liver cells. The method can further comprise detecting and comparing the amplifying marker induced biosensor response of the liver cells in the presence and absence of a molecule.

The period of time between contacting the immobilized liver cells with a molecule and contacting the molecule-treated liver cells with an amplifying marker can comprise, for example, at least one of from about seconds to about minutes, from about minutes to about hours, from about days to about weeks, or combinations thereof. In embodiments, the period of time between contacting the liver cells with a molecule and contacting the molecule-treated cells with an amplifying marker can comprise, for example, one to four hours.

5. Direct Method for Characterizing Toxicity

In general, the central role played by the liver in the metabolism of chemicals also can make it susceptible to toxin induced injury. For example, acetaminophen overdose can cause the liver to metabolize acetaminophen into a toxic intermediate called N-acetyl-p-benzoquinoemine (NAPQI). Unfortunately, because toxicity often requires the formation of a metabolite by the liver, toxicity screenings can be ineffective if performed on cells that are not metabolically active.

Thus, the disclosure provides methods for directly characterizing the toxicity of a molecule to metabolically active liver cells, such as primary liver cells, using, for example, a Corning® Epic® biosensor system.

In embodiments the disclosure provides a method for directly characterizing the toxicity of a molecule to liver cells, the method comprising:

providing a biosensor having liver cells immobilized on the biosensor's surface, wherein the immobilized liver cells are immobilized between nanoscale or microscale clusters of a first extra cellular matrix material coated on the biosensor's surface and an overlay of a second extra cellular matrix material, and wherein the immobilized liver cells retain at least a portion of their metabolic functions;

contacting the immobilized liver cells with a molecule; and detecting and comparing the molecule induced biosensor response of the liver cells in the presence and absence of known liver toxicants.

In embodiments the first and second extra cellular matrix materials comprise essentially any type of biological material found in tissue and outside of cells that is able to provide structural support to cells. The extracellular matrix material can be a protein, a polysaccharide, or a glycoprotein. In embodiments, the extracellular matrix material can be, for example, a collagen (e.g., collagen I or collagen IV), fibronectin, Matrigel™, or a combination thereof. In particular embodiments, the first extra cellular matrix material comprises collagen I and the second extra cellular matrix material comprises Matrigel™.

In embodiments the liver cells comprise at least one of: a primary liver cell, a transformed liver cell, an immortalized liver cell, or a combination thereof.

6. Method for Culturing Cells on a Biosensor

In general, hepatocytes can represent a physiologically relevant model for drug toxicity screening. However, extracellular matrix coatings are necessary to maintain the viability and metabolic activity of hepatocytes. As a result, most in vitro hepatocyte culture systems are based on three dimensional cultures, which generally are not amenable to detection by biosensors due to their relatively short sensing volume and/or their sensitivity to cellular changes at or near the biosensor surface.

Thus, the disclosure provides a method of culturing metabolically active liver cells on a biosensor. The use of a biosensor surface having a coating of clusters of an extracellular matrix material can provide appropriate topology for liver cell metabolic activity, and thus can allow for robust detection of molecular toxicity in a biosensor cellular assay.

In embodiments the disclosure provides a method of culturing metabolically active liver cells on a biosensor, the method comprising:

applying a first aqueous solution comprising a first extracellular matrix material onto the surface of a biosensor;

drying the first aqueous solution, wherein the drying results in an coating on the surface comprising nanoscale or microscale clusters of the first extracellular matrix material to form a coated biosensor surface;

culturing a liver cell onto the coated biosensor surface, and applying a second extracellular matrix material into the medium covering the cultured cell, wherein the second extracellular matrix material forms an overlay with the liver cells on the surface of the biosensor.

In embodiments, the first and second extra cellular matrix materials comprise essentially any type of biological material found in tissue and outside of cells that is able to provide structural support to cells. The extracellular matrix material can be a protein, a polysaccharide, or a glycoprotein. In embodiments, the extracellular matrix material can be, for example, a collagen (e.g., collagen I or collagen IV), fibronectin, Matrigel™, or a combination thereof. In particular embodiments, the first extra cellular matrix material comprises collagen I and the second extra cellular matrix material comprises Matrigel™.

In embodiments, the first aqueous solution can comprise the first extracellular matrix material in an amount, for example, in the range of about 1 μg/ml to about 100 μg/ml, in the range of about 5 μg/ml to about 50 μg/ml, or of about 10 μg/ml.

In embodiments, the drying can comprises drying under a vacuum for a period of time in the range of about 1 hour to about 24 hours, in the range of about 12 hours to about 24 hours, or in the range of about 16 hours to about 24 hours. This drying period can take advantage of the slow self-assembly of the extra cellular matrix materials, and thus can result in an un-even coating consisting of a series of clusters, as shown by fluorescently tagged antibody staining or atomic force imaging (data not shown).

In embodiments, the second aqueous solution can comprise the second extracellular matrix material in an amount, for example, in the range of about 0.01% to about 1% by weight, in the range of about 0.05% to about 0.5%, or of about 0.1%.

In embodiments, the liver cells comprise at least one of: a primary liver cell, a transformed liver cell, an immortalized liver cell, or a combination thereof.

7. Biosensor Liver Culture System

Furthermore, the disclosure provides a biosensor liver culture system wherein the immobilized liver cells retain at least a portion of their metabolic function.

In embodiments the disclosure provides a biosensor liver culture system, the system comprising:

a biosensor surface coated with nanoscale or microscale clusters of a first extracellular matrix material;

a liver cell immobilized onto the biosensor surface wherein the immobilized liver cells comprise at least one of: a primary liver cell, a transformed liver cell, an immortalized liver cell, or a combination thereof; and an overlay comprising a second extracellular matrix material, wherein the sandwiched liver cells retain at least a portion of their metabolic function.

In embodiments, the biosensor surface can comprise a metallic film. For example, the biosensor surface can comprise a gold film.

In embodiments the first and second extra cellular matrix materials comprise essentially any type of biological material found in tissue and outside of cells that is able to provide structural support to cells. The extracellular matrix material can be a protein, a polysaccharide, or a glycoprotein. In embodiments, the extracellular matrix material can be, for example, a collagen (e.g., collagen I or collagen IV), fibronectin, Matrigel, or a combination thereof. In particular embodiments, the first extra cellular matrix material comprises collagen I and the second extra cellular matrix material comprises Matrigel.

In embodiments the overlay can comprise the second extracellular matrix material in an amount, for example, in the range of about 0.01% to about 1% by weight, in the range of about 0.05% to about 0.5%, or of about 0.1%.

FIG. 1 shows a side view of a biosensor liver cell culture system (100). The biosensor liver cell culture system comprises a biosensor having a surface coating comprising of a series of clusters of an ECM material (160) or ECM mixture (160), a layer of liver cells (140), and a second ECM material (170). The liver cell is sandwiched between the biosensor surface (160) and the second ECM material (170). The biosensor consists of a substrate (120) wherein a grating structure is embedded (125) and a waveguide film (130). For optical biosensors, the biosensor may emit a short evanescent wave (135) extended away from the biosensor surface creating a sensing zone that is approximately 150-200 nm from the sensor surface, when an optical biosensor is used. The cells are contacted with the surface through adhesion complexes (150). Cells respond to a compound stimulation with dynamic mass redistribution in the direction perpendicular to the biosensor surface (145), when an optical biosensor is used. The DMR signal can be detected with a light detector consisting of an illumination light (110), and the optical contents of the reflected light (115) can be recorded with a receiver system and used as an indicator for the DMR signal.

8. Biosensors and Biosensor Assays

Label-free cell-based assays generally employ a biosensor to monitor a compound-induced response in living cells. The compound can be naturally occurring or synthetic, and can be purified or unpurified mixture. A biosensor typically utilizes a transducer such as an optical, electrical, calorimetric, acoustic, magnetic, or like transducer, to convert a molecular recognition event or a compound-induced change in cells contacted with the biosensor into a quantifiable signal. These label-free biosensors can be used for molecular interaction analysis, which involves characterizing how molecular complexes form and disassociate over time, or for cellular response, which involves characterizing how cells respond to stimulation. The biosensors that are applicable to the present invention can include, for example, optical biosensor systems such as surface plasmon resonance (SPR) and resonant waveguide grating (RWG) biosensors, resonant mirrors, ellipsometers, or electric biosensor systems such as bio-impedance systems.

a) SPR Biosensors and Systems

SPR relies on a prism to direct a wedge of polarized light, covering a range of incident angles, into a planar glass substrate bearing an electrically conducting metallic film (e.g., gold) to excite surface plasmons. The resultant evanescent wave interacts with, and is absorbed by, free electron clouds in the gold layer, generating electron charge density waves (i.e., surface plasmons) and causing a reduction in the intensity of the reflected light. The resonance angle at which this intensity minimum occurs is a function of the refractive index of the solution close to the gold layer on the opposing face of the sensor surface.

b) RWG Biosensors and Systems

An RWG biosensor can include, for example, a substrate (e.g., glass), a waveguide thin film with an embedded grating structure, and a cell layer. The RWG biosensor utilizes the resonant coupling of light into a waveguide by means of a diffraction grating, leading to total internal reflection at the solution-surface interface, which in turn creates an electromagnetic field at the interface. This electromagnetic field is evanescent in nature, meaning that it decays exponentially from the sensor surface; the distance at which it decays to 1/e of its initial value is known as the penetration depth and is a function of the design of a particular RWG biosensor, but is typically on the order of about 200 nm. This type of biosensor exploits such evanescent waves to characterize ligand-induced alterations of a cell layer at or near the sensor surface.

RWG instruments can be subdivided into systems based on angle-shift or wavelength-shift measurements. In a wavelength-shift measurement, polarized light covering a range of incident wavelengths with a constant angle is used to illuminate the waveguide; light at specific wavelengths is coupled into and propagates along the waveguide. Alternatively, in angle-shift instruments, the sensor is illuminated with monochromatic light and the angle at which the light is resonantly coupled is measured. The resonance conditions are influenced by the cell layer (e.g., cell confluency, adhesion and status) which is in direct contact with the surface of the biosensor. When a ligand or an analyte interacts with a cellular target (e.g., a GPCR, a kinase) in living cells, any change in local refractive index within the cell layer can be detected as a shift in resonant angle (or wavelength).

The Corning® Epic® system uses RWG biosensors for label-free biochemical or cell-based assays (Corning Inc., Corning, N.Y.). The Epic® System consists of an RWG plate reader and SBS (Society for Biomolecular Screening) standard microtiter plates. The detector system in the plate reader exploits integrated fiber optics to measure the shift in wavelength of the incident light, as a result of ligand-induced changes in the cells. A series of illumination-detection heads are arranged in a linear fashion, so that reflection spectra are collected simultaneously from each well within a column of a 384-well microplate. The whole plate is scanned so that each sensor can be addressed multiple times, and each column is addressed in sequence. The wavelengths of the incident light are collected and used for analysis. A temperature-controlling unit can be included in the instrument to minimize spurious shifts in the incident wavelength due to the temperature fluctuations. The measured response represents an averaged response of a population of cells.

c) Electrical Biosensors and Systems

Electrical biosensors consist of a substrate (e.g., plastic), an electrode, and a cell layer. In this electrical detection method, cells are cultured on small gold electrodes arrayed onto a substrate, and the system's electrical impedance is followed with time. The impedance is a measure of changes in the electrical conductivity of the cell layer. Typically, a small constant voltage at a fixed frequency or varied frequencies is applied to the electrode or electrode array, and the electrical current through the circuit is monitored over time. The ligand-induced change in electrical current provides a measure of cell response. Impedance measurement for whole cell sensing was first realized in 1984. Since then, impedance-based measurements have been applied to study a wide range of cellular events, including cell adhesion and spreading, cell micromotion, cell morphological changes, and cell death. Classical impedance systems suffer from high assay variability due to use of a small detection electrode and a large reference electrode. To overcome this variability, the latest generation of systems, such as the CellKey system (MDS Sciex, South San Francisco, Calif.) and RT-CES (ACEA Biosciences Inc., San Diego, Calif.), utilize an integrated circuit having a microelectrode array.

d) High Spatial Resolution Biosensor Imaging Systems

Optical biosensor imaging systems, including SPR imaging systems, ellipsometry imaging systems, and RWG imaging systems, offer high spatial resolution, and can be used in the present invention. For example, SPR Imager®II (GWC Technologies Inc) uses prism-coupled SPR, and takes SPR measurements at a fixed angle of incidence, and collects the reflected light with a CCD camera. Changes on the surface are recorded as reflectivity changes. Thus, SPR imaging collects measurements for all elements of an array simultaneously.

Alternatively a swept wavelength optical interrogation system based on an RWG biosensor for imaging-based applications can be used. In this system, a fast tunable laser source is used to illuminate a sensor or an array of RWG biosensors in a microplate format. The sensor spectrum can be constructed by detecting the optical power reflected from the sensor as a function of time as the laser wavelength scans, and analysis of the measured data with computerized resonant wavelength interrogation modeling results in the construction of spatially resolved images of biosensors having immobilized receptors or a cell layer. The use of an image sensor naturally leads to an imaging based interrogation scheme. 2 dimensional label-free images can be obtained without moving parts.

Alternatively, an angular interrogation system with transverse magnetic or p-polarized $TM_0$ mode can be used. This system consists of a launch system for generating an array of light beams such that each illuminates a RWG sensor with a dimension of approximately 200 μM×3000 μm or 200 μm×2000 μm, and a CCD camera-based receive system for recording changes in the angles of the light beams reflected from these sensors. The arrayed light beams are obtained by means of a beam splitter in combination with diffractive optical lenses. This system allows up to 49 sensors (in a 7×7 well sensor array) to be simultaneously sampled at every 3 seconds or a whole sensor microplate to be sampled at every 10 sec or so.

Alternatively, a scanning wavelength interrogation system can be used. In this system, a polarized light covering a range of incident wavelengths with a constant angle is used to illuminate and scan across a waveguide grating biosensor, and the reflected light at each location can be recorded simultaneously. Through scanning, a high resolution image across a biosensor can be achieved.

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

e) Biosensor Cellular Assays

The cellular response to stimulation through a cellular target can be encoded by the spatial and temporal dynamics of downstream signaling networks. For this reason, monitoring the integration of cell signaling in real time can provide physiologically relevant information that is useful in understanding cell biology and physiology.

Optical biosensors including resonant waveguide grating (RWG) biosensors, can detect an integrated cellular response related to dynamic redistribution of cellular matters, thus providing a non-invasive means for studying cell signaling. All optical biosensors are common in that they can measure changes in local refractive index at or very near the sensor surface. In principle, almost all optical biosensors are applicable for cell sensing, as they can employ an evanescent wave to characterize ligand-induced change in cells. The evanescent-wave is an electromagnetic field, created by the total internal reflection of light at a solution-surface interface, which typically extends a short distance (~hundreds of nanometers) into the solution at a characteristic depth known as the penetration depth or sensing volume.

Recently, theoretical and mathematical models have been developed that describe the parameters and nature of optical signals measured in living cells in response to stimulation with ligands. These models, based on a 3-layer waveguide system in combination with known cellular biophysics, link the ligand-induced optical signals to specific cellular processes mediated through a receptor.

Because biosensors measure the average response of the cells located at the area illuminated by the incident light, a highly confluent layer of cells can be used to achieve optimal assay results. Due to the large dimension of the cells as compared to the short penetration depth of a biosensor, the sensor configuration is considered as a non-conventional three-layer system: a substrate, a waveguide film with a grating structure, and a cell layer. Thus, a ligand-induced change in effective refractive index (i.e., the detected signal) can be, to first order, directly proportional to the change in refractive index of the bottom portion of the cell layer:

$$\Delta N = S(C) \Delta n_c$$

where $S(C)$ is the sensitivity to the cell layer, and $\Delta n_c$ the ligand-induced change in local refractive index of the cell layer sensed by the biosensor. Because the refractive index of a given volume within a cell is largely determined by the concentrations of bio-molecules such as proteins, $\Delta n_c$ can be assumed to be directly proportional to ligand-induced change in local concentrations of cellular targets or molecular assemblies within the sensing volume. Considering the exponentially decaying nature of the evanescent wave extending away from the sensor surface, the ligand-induced optical signal is governed by:

$$\Delta N = S(C) \alpha d \sum_i \Delta C_i \left[ e^{\frac{-z_i}{\Delta Z_C}} - e^{\frac{-z_{i+1}}{\Delta Z_C}} \right]$$

where $\Delta Z_c$ is the penetration depth into the cell layer, α the specific refraction increment (about 0.18/mL/g for proteins), z, the distance where the mass redistribution occurs, and d an imaginary thickness of a slice within the cell layer. Here the cell layer is divided into an equal-spaced slice in the vertical direction. The equation above indicates that the ligand-induced optical signal is a sum of mass redistribution occurring at distinct distances away from the sensor surface, each with an unequal contribution to the overall response. Furthermore, the detected signal, in terms of wavelength or angular shifts, is primarily sensitive to mass redistribution occurring perpendicular to the sensor surface. Because of its dynamic nature, it also is referred to as dynamic mass redistribution (DMR) signal.

9. Cells and Biosensors

Cells rely on multiple cellular pathways or machineries to process, encode and integrate the information they receive. Unlike the affinity analysis with optical biosensors that specifically measures the binding of analytes to a protein target, living cells are much more complex and dynamic.

To study cell signaling, cells can be brought into contact with the surface of a biosensor, which can be achieved through cell culture. These cultured cells can be attached onto the biosensor surface through three types of contacts: focal contacts, close contacts and extracellular matrix contacts, each with its own characteristic separation distance from the surface. As a result, the basal cell membranes are generally located away from the surface by ~10-100 nm. For this reason, biosensors are able to sense the bottom portion of cells.

Cells, in many cases, exhibit surface-dependent adhesion and proliferation. In order to achieve robust cell assays, the biosensor surface can require a coating to enhance cell adhesion and proliferation. However, the surface properties can have a direct impact on cell biology. For example, surface-bound ligands can influence the response of cells, as can the mechanical compliance of a substrate material, which dictates how it will deform under forces applied by the cell. Due to differing culture conditions (time, serum concentration, confluency, etc.), the cellular status obtained can be distinct from one surface to another, and from one condition to another. Thus, special efforts to control cellular status can be necessary in order to develop biosensor-based cell assays.

Cells are dynamic objects with relatively large dimensions—typically in the range of tens of microns. Even without stimulation, cells constantly undergo micromotion—a dynamic movement and remodeling of cellular structure, as observed in tissue culture by time lapse microscopy at the sub-cellular resolution, as well as by bio-impedance measurements at the nanometer level.

Under un-stimulated conditions cells generally produce an almost net-zero DMR response as examined with a RWG biosensor. This is partly because of the low spatial resolution of optical biosensors, as determined by the large size of the laser spot and the long propagation length of the coupled light. The size of the laser spot determines the size of the area studied—and usually only one analysis point can be tracked at a time. Thus, the biosensor typically measures an averaged response of a large population of cells located at the light incident area. Although cells undergo micromotion at the single cell level, the large populations of cells give rise to an average net-zero DMR response. Furthermore, intracellular macromolecules are highly organized and spatially restricted to appropriate sites in mammalian cells. The tightly controlled localization of proteins on and within cells determines specific cell functions and responses because the localization allows cells to regulate the specificity and efficiency of proteins interacting with their proper partners and to spatially separate protein activation and deactivation mechanisms. Because of this control, under un-stimulated conditions, the local mass density of cells within the sensing volume can reach an equilibrium state, thus leading to a net-zero optical response. In order to achieve a consistent optical response, the cells examined can be cultured under conventional culture conditions for a period of time such that most of the cells have just completed a single cycle of division.

Living cells have exquisite abilities to sense and respond to exogenous signals. Cell signaling was previously thought to function via linear routes where an environmental cue would trigger a linear chain of reactions resulting in a single well-defined response. However, research has shown that cellular responses to external stimuli are much more complicated. It has become apparent that the information that cells receive can be processed and encoded into complex temporal and spatial patterns of phosphorylation and topological relocation of signaling proteins. The spatial and temporal targeting of proteins to appropriate sites can be crucial to regulating the specificity and efficiency of protein-protein interactions, thus dictating the timing and intensity of cell signaling and responses. Pivotal cellular decisions, such as cytoskeletal reorganization, cell cycle checkpoints and apoptosis, depend on the precise temporal control and relative spatial distribution of activated signal-transducers. Thus, cell signaling mediated through a cellular target such as G protein-coupled receptor (GPCR) typically proceeds in an orderly and regulated manner, and consists of a series of spatial and temporal events, many of which lead to changes in local mass density or redistribution in local cellular matters of cells. These changes or redistribution, when occurring within the sensing volume, can be followed directly in real time using optical biosensors 10. Biosensor Parameters A label-free biosensor such as RWG biosensor or bio-impedance biosensor is able to follow in real time ligand-induced cellular response. The non-invasive and manipulation-free biosensor cellular assays do not require prior knowledge of cell signaling. The resultant biosensor signal contains high information relating to receptor signaling and ligand pharmacology. Multi-parameters can be extracted from the kinetic biosensor response of cells upon stimulation. These parameters include, but not limited to, the overall dynamics, phases, signal amplitudes, as well as kinetic parameters including the transition time from one phase to another, and the kinetics of each phase (see Fang, Y., and Ferrie, A. M. (2008) "label-free optical biosensor for ligand-directed functional selectivity acting on β2 adrenoceptor in living cells". FEBS Lett. 582, 558-564; Fang, Y., et al., (2005) "Characteristics of dynamic mass redistribution of EGF receptor signaling in living cells measured with label free optical biosensors". Anal. Chem., 77, 5720-5725; Fang, Y., et al., (2006) "Resonant waveguide grating biosensor for living cell sensing". Biophys. J., 91, 1925-1940).

EXAMPLES

A. Experimental Procedures

1. Materials

Rifampin, SB203580, hydrogen peroxide, acetaminophen, and thrombin were obtained from Sigma Chemical Co. (St. Louis, Mo.). Matrigel™ was obtained from BD Bioscience. Corning® Epic® 384 biosensor microplates cell culture compatible were obtained from Corning Inc. (Corning, N.Y.). Collagen I coated 96-well plates were obtained from BD Bioscience (Cat#354407), and used as a control.

2. Coating of Biosensor Microplates

Collagen coating of the biosensor microplates was achieved by dispensing 10 μl collagen I (10 μg/ml) into each well, and followed by slow drying over night under controlled vacuum condition. This coating process takes advantage of slow self-assembly of collagen I, and results in an un-even coating consisting of a series of clusters of collagen I, thus providing microscale or nanoscale topology of ECM materials to liver cells to form Epic® 384well biosensor microplate collagen coated.

3. Sandwich Primary Liver Cell Culture

Human primary hepatocytes were purchased from Xeno-Tech (H1500.H15A+Lot No. 770). Cells were thawed and purified using Xenotech Hepatocyte isolation kit (Cat#: K2000) according to the manufacturer's instructions. Cells (50,000/well) were plated in either Epic 384well collagen I coated biosensor microplate or the BD Bioscience collagen coated 96-well microplate using Galactose-free MFE Plating Medium (Corning Inc.) containing 10% FBS on Day 1. The medium was changed to MFE Maintenance Medium containing 10% FBS with 0.25 mg/ml Matrigel (BD Bioscience, Cat#356234) on Day 2. Cells were incubated at 37° C. with 5% $CO_2$ from Day 1 to Day 8. From Day 5, cells were treated with 10 μM rifampin (Cat# R3501, Sigma-Aldrich Inc.) or equal volume of DMSO for 72 hours. On Day 8, CYP3A4 assay was performed using P450-Glo™ CYP3A4 Assay kit (Cat# V8902, Promega), and the assay results were reported as fold of induction after cell number normalization. Cell number was normalized using CytoTox 96® Non-Radioactive Cytotoxicity Assay (Cat#G1780, Promega).

4. Optical Biosensor System and Cell Assays

A beta version of Corning® Epic® wavelength interrogation system was used for whole cell sensing. This system consists of a temperature-control unit, an optical detection unit, and an on-board liquid handling unit with robotics. The detection unit is centered on integrated fiber optics, and enables kinetic measures of cellular responses with a time interval of ~15 sec. All molecule compound additions were done simply through pippetting using the onboard liquid handler.

The RWG biosensor exploits its evanescent wave to measure ligand-induced DMR signals in cells. The evanescent wave extends into the cells and exponentially decays over distance, leading to a characteristic sensing volume of ~150 nm, implying that any optical response mediated through the receptor activation only represents an average over the portion of the cell that the evanescent wave is sampling. The aggregation of many cellular events downstream the receptor activation determines the kinetics and amplitudes of a ligand-induced DMR.

For biosensor cellular assays, a 2-min baseline was first established. Compound solutions were then transferred into the sensor plate having cells maintained in Hanks balanced salt (HBSS) solution containing 20 mM Hepes, pH 7.1. The cell responses were recorded continuously. All studies were carried out at controlled temperature (26° C.). At least two independent sets of experiments, each with at least sixteen replicates, were carried out for each measurement. The assay coefficient of variation was found to be <10%.

B. Example 1

Primary Liver Cells Restore their Metabolic Function Once Cultured on the Biosensor Sandwich Culture System Human primary hepatocytes obtained were directly used to culture on the sensor surface having a series of clusters of collagen I. After several hours to overnight culture, a solution overlay of primary liver cells with 0.1% matrigel in the culture medium was applied. As a result, the primary liver cells formed a monolayer sandwiched between the collagen I presenting biosensor surface and the second ECM material (i.e., matrigel).

To test the metabolic function of primary liver cells cultured on the biosensor surface using the biosensor liver cell sandwich culture system, rifampin induction experiments were carried out with 5 days of culture using the P450-Glo™ CYP3A4 Assay kit according to the protocol recommended by the supplier. After cell number normalization, the fold of induction was calculated. For comparison, the same lot of primary liver cells were cultured onto the collagen I coated BD Bioscience's 96 well microplate and also sandwiched using the matrigel solution overlay. Two different conditions for rifampin induction were examined—cells were treated with rifampin in the absence and presence of 0.5% DMSO throughout the induction process.

Figure 2:
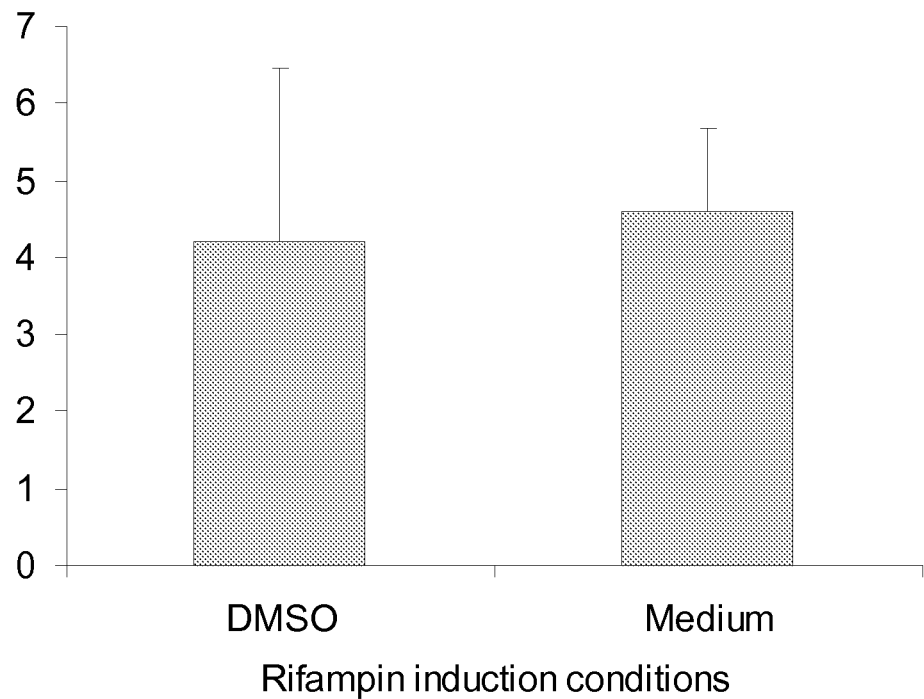
FIG. 2A shows rifampin induction results of primary liver cells cultured on a collagen I coated tissue culture surface, both in the absence and presence of 0.5% dimethyl sulfoxide (DMSO), in embodiments of the disclosure.
FIG. 2B shows primary liver cells cultured on a biosensor surface having a series of clusters of collagen I, both in the absence and presence of 0.5% dimethyl sulfoxide (DMSO), in embodiments of the disclosure.
Figure 2:
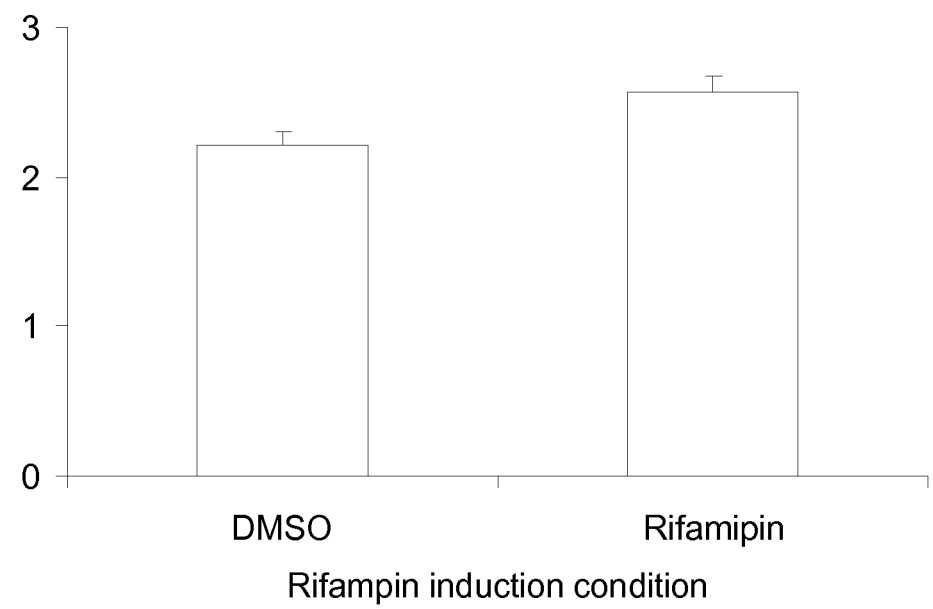

FIGS. 2A and 2B show plots of the fold of induction. The results show that on both culture systems, rifampin treatment led to an increase of CYP function. The fold of induction in the absence and presence of DMSO was comparable, indicating that the cultured primary liver cells restored their metabolic function. Furthermore, the fold of induction is higher on the BD Bioscience's regular collagen I-matrigel sandwich system than that on the biosensor sandwich system. However, the assay is much more reproducible on the biosensor sandwich system (FIG. 2b), suggesting that the microscale or nanoscale topology of collagen I clusters on the biosensor surfaces is important to regulate the metabolic functions of primary liver cells.

C. Example 2

Hydrogen Peroxide LED to Apoptosis of Primary Liver Cells Cultured on the Biosensor Sandwich System Reactive oxygen species (ROS) such as superoxide anion radical, hydrogen peroxide ($H_2O_2$) and hydroxyl radical are generated endogenously through respiration in the mitochondria. In addition to the leakage of ROS from the mitochondria, a number of exogenous oxidizing agents including ionizing radiation can react with cellular components such as proteins, lipids and nucleic acids. Reactive oxygen species produce oxidized bases, deoxyribose lesions and DNA strand breaks in mammalian cells. It is believed that oxidized bases, such as 8-hydroxyguanine, are predominantly repaired by a base excision repair pathway. ROS can also directly induce sugar lesions by hydrogen abstraction from deoxyribose, frequently producing DNA strand breaks. A bimodal $H_2O_2$ dose-response relationship in cell toxicity and mitochondrial DNA damage has been known for Chinese hamster ovary (CHO) cells. Furthermore, it has been demonstrated that $H_2O_2$ causes single-strand breaks in purified DNA in the presence of iron and induces mitochondrial DNA damage in CHO cells with a biphasic dose-response curve.

Reactive oxygen species, including $H_2O_2$, play an important role in the tumor promotion process. The involvement of reactive oxygen species, particularly $H_2O_2$, in the tumor promotion process is supported by both in vivo and in vitro studies. $H_2O_2$ is capable of promoting neoplastic transformation in several two-stage transformation systems, including rat urothelial cells, murine myeloid progenitor cells, mouse epidermal cells and mouse embryo fibroblasts. In vivo studies also suggest that $H_2O_2$ is a mouse skin tumor promoter. Indirect evidence supporting a role for ROS, including $H_2O_2$, in tumor promotion, is that inhibition of ROS generated by tumor promoters profoundly reduces transformation. An antioxidant fraction of Chinese green tea can inhibit the production of $H_2O_2$ and in cultured lung cells it can inhibit oxidant-induced DNA strand breaks. Furthermore, the production of ROS and $H_2O_2$ is a common feature of tumor promoters such as TPA, TCDD, UV, peroxisome proliferators, steroidal estrogens, phenobarbital, chlordane and aroclor. For example, $H_2O_2$ serves as a tumor promoter in rat liver epithelial T51B cells and that tumor promotion by $H_2O_2$ may involve the interruption of gap junction communication and the induction of immediate early genes. Therefore, ROS, including $H_2O_2$, may play a critical role in the tumor promotion process.

Pathological events such as inflammation, ischemia/reperfusion injury, and atherosclerosis are also accompanied by production of high quantities of reactive oxygen species within the vasculature. Depending on the source of ROS generation and the concentration and duration of exposure to oxidants, endothelial cell responses to ROS vary from proliferation and survival to dysfunction and cell death. The molecular signaling pathways that govern these responses are just beginning to emerge and include activation of Akt, eNOS, Src-like kinases, growth factor receptors, and MAP kinases. For instance, Src-kinases, eNOS, and Ras are activated in response to ROS. In addition, ROS have been shown to cause the transactivation of epidermal growth factor receptor (EGFR).

Figure 3:
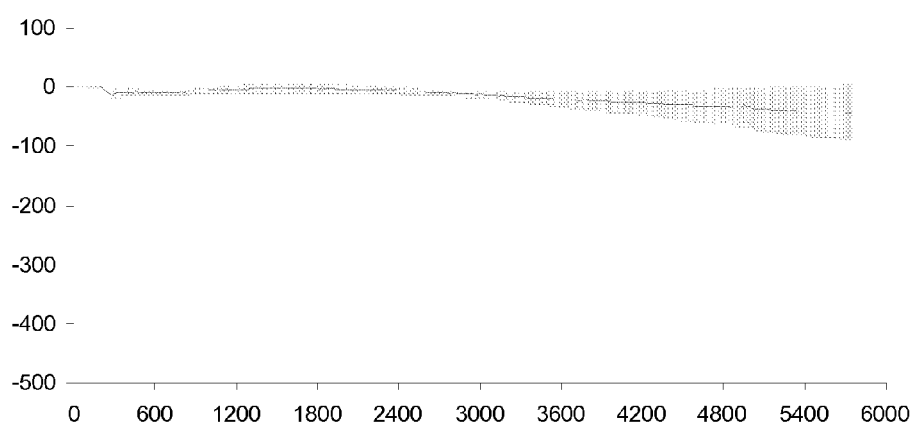
FIG. 3A shows a DMR signal of primary liver cells in a biosensor liver cell culture system induced with 1 mM hydrogen peroxide, in embodiments of the disclosure.
FIG. 3B shows a DMR signal of primary liver cells in a biosensor liver cell culture system induced with 5 mM hydrogen peroxide, in embodiments of the disclosure.
Figure 3:
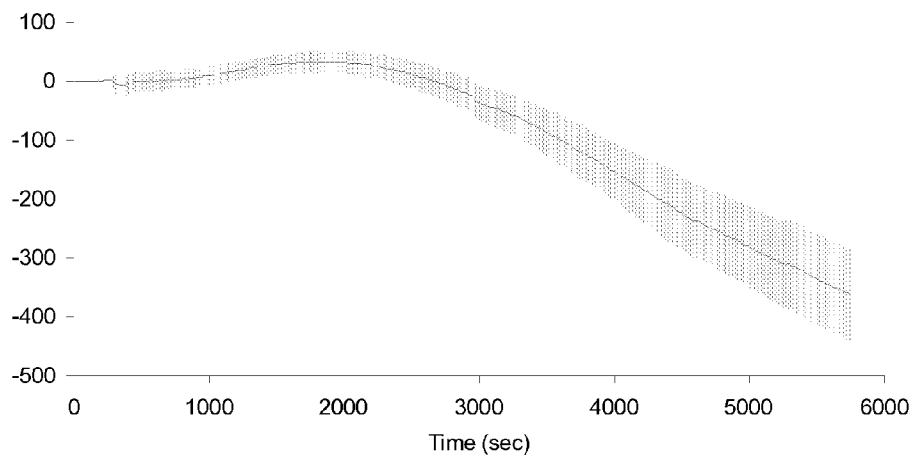

Hydrogen peroxide is toxic to any cells, and can cause cell apoptosis in a dose-dependent manner. FIGS. 3A and 3B show the real time kinetic DMR responses of the primary liver cells cultured using the present biosensor sandwich culture system upon exposure to $H_2O_2$ at two different doses, 1 mM (FIG. 3A) and 5 mM (FIG. 3B). Each kinetic DMR response represents an average of 8 replicates, in which the error bar indicates the standard deviation. When cells on the biosensor surface undergo apoptosis, a significant loss (i.e., a negative DMR signal) is expected. At 1 mM, $H_2O_2$ did not trigger any significant change in local biomass with the sensing volume or detection zone of the biosensor, indicating that the primary liver cells are not killed by $H_2O_2$. Conversely, 5 mM $H_2O_2$ led to a significant negative DMR (N-DMR) signal, indicating the apoptosis of the cultured primary liver cells. The onset time for the N-DMR signal to occur was found to be around 30 min after treatment with 5 mM $H_2O_2$.

D. Example 3

Hydrogen Peroxide Amplifies the Toxicity of Rifampin Acting on Primary Liver Cells Cultured on the Biosensor Sandwich System The human body identifies almost all drugs as foreign substances (i.e. xenobiotics) and subjects them to various chemical processes (i.e. metabolism) to make them suitable for elimination. This involves chemical transformations to (a) reduce fat solubility and (b) to change biological activity. Although almost all tissues in the body have some ability to metabolize chemicals, smooth endoplasmic reticulum in liver is the principal "metabolic clearing house" for both endogenous chemicals (e.g., cholesterol, steroid hormones, fatty acids, and proteins), and exogenous substances (e.g. drugs).

Drug metabolism is usually divided into two phases: phase 1 and phase 2. Phase 1 reactions are thought to prepare a drug for phase 2. However, many molecules can be metabolized by phase 2 directly. Phase 1 reactions involve oxidation, reduction, hydrolysis, hydration and many other rare chemical reactions. These processes tend to increase water solubility of the drug and can generate metabolites which are more chemically active and potentially toxic. Most phase 2 reactions take place in cytosol and involve conjugation with endogenous compounds via transferase enzymes. Chemically active phase 1 products are rendered relatively inert and suitable for elimination by this step.

A group of enzymes located in the endoplasmic reticulum, known as cytochrome P-450, is the most important family of metabolizing enzyme in liver. Cytochrome P-450 is the terminal oxidase component of an electron transport chain. It is not a single enzyme, but rather consists of a family of 50 closely related isoforms, six of them metabolize 90% of drugs. There is a tremendous diversity of individual P-450 gene products and this heterogeneity allows the liver to perform oxidation on a vast array of chemicals (including almost all drugs) in phase 1. The three important characteristics of the P450 system, genetic diversity, change in enzyme activity and competitive inhibition, have roles in drug induced toxicity. Many substances can influence P-450 enzyme mechanism. Drugs interact with the enzyme family in several ways. Drugs that modify Cytochrome P-450 enzyme are referred to as either inhibitors or inducers. CYP inhibitors block the metabolic activity of one or several P-450 enzymes. This effect usually occurs immediately. On the other hand, inducers increase P-450 activity by increasing its synthesis. Depending on inducing a drug's half life, there is usually a delay before enzyme activity increases.

The central role played by liver in the clearance and transformation of chemicals also makes it susceptible to drug induced injury, termed as hepatotoxicity. Certain medicinal agents, when taken in overdoses and sometime even when introduced within therapeutic ranges, may injure the organ. Other chemical agents such as those used in laboratories and industries, natural chemicals (e.g. microcystins) and herbal remedies also can induce hepatotoxicity. Chemicals that cause liver injury are called hepatotoxins.

More than 900 drugs have been implicated in causing liver injury and it is the most common reason for a drug to be withdrawn from the market. Chemicals often cause subclinical injury to liver which manifest only as abnormal liver enzyme tests. Drug induced liver injury is responsible for 5% of all hospital admissions and 50% of all acute liver failures.

Several mechanisms are responsible for either inducing hepatic injury or worsening the damage process. Many chemicals damage mitochondria, an intracellular organelle that produces energy. Its dysfunction releases excessive amount of oxidants which in turn injures hepatic cells. Activation of some enzymes in the cytochrome P-450 system such as CYP2E1 also leads to oxidative stress. Injury to hepatocyte and bile duct cells lead to accumulation of bile acid inside the liver. This promotes further liver damage. Non-parenchymal cells such as Kupffer cells, fat storing stellate cells and leukocytes (i.e. neutrophil and monocyte) also have a role in the mechanism.

Adverse drug reactions are classified as type A (intrinsic or pharmacological) or type B (idiosyncratic). Type A drug reactions account for 80% of all toxicities. Drugs or toxins that have a pharmacological (type A) hepatotoxicity are those that have predictable dose-response curves (higher concentrations cause more liver damage) and well characterized mechanisms of toxicity such as directly damaging liver tissue or blocking a metabolic process. As in the case of acetaminophen overdose, this type of injury occurs shortly after some threshold for toxicity is reached. Idiosyncratic injury occurs without warning, when agents cause non-predictable hepatotoxicity in susceptible individuals which is not related to dose and has a variable latency period. This type of injury does not have a clear dose-response or temporal relationship, and most often does not have predictive models. Idiosyncratic hepatotoxicity has led to the withdrawal of several drugs from market even after rigorous clinical testing as part of the FDA approval process was completed; Troglitazone (Rezulin®) and trovafloxacin (Trovan®) are two prime examples of idiosyncratic hepatotoxins. The development of anticoagulant ximelagatran (Exanta®) was discontinued for concerns of liver damage.

Rifampin is a semisynthetic antibiotic derived from a form of rifamycin that interferes with the synthesis of RNA and is used to treat bacterial and viral diseases. Rifampicin is typically used to treat *Mycobacterium* infections, including tuberculosis and leprosy; and also has a role in the treatment of methicillin-resistant *Staphylococcus aureus* (MRSA) in combination with fusidic acid. It also is used in prophylactic therapy against *Neisseria meningitidis* (meningococcal) infection.

Rifampicin inhibits DNA-dependent RNA polymerase in bacterial cells by binding its beta-subunit, thus preventing transcription of messenger RNA (mRNA) and subsequent translation to proteins. Its lipophilic nature makes it a good candidate to treat the meningitis form of tuberculosis, which requires distribution to the central nervous system and penetration through the blood-brain barrier.

However, rifampin exhibits adverse effects that are chiefly related to the drug's hepatotoxicity, and patients receiving rifampicin often undergo liver function tests including aspartate aminotransferase (AST). Rifampicin is a potent inducer of hepatic cytochrome P450 enzymes (such as CYP2D6 and CYP3A4), and will increase the metabolism of many drugs that are cleared by the liver through this enzyme system. This results in numerous drug interactions such as reduced efficacy of hormonal contraception. For example, rifampin can enhance the metabolism of endogenous substrates including adrenal hormones, thyroid hormones, and vitamin D.

Figure 4:
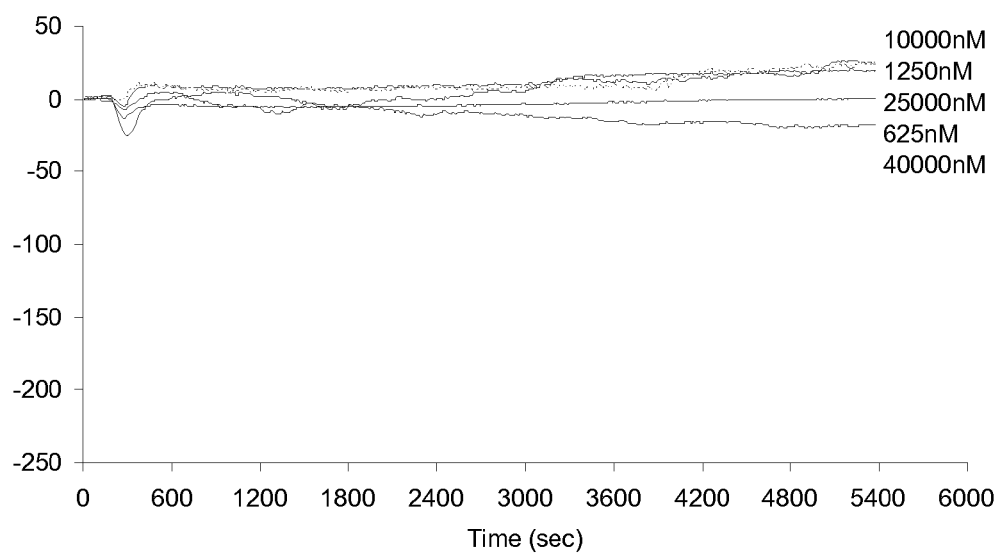
FIG. 4A shows a DMR signal of primary liver cells in a biosensor liver cell culture system induced with rifampin at doses in the range of 625 nM to 40000 nM, in embodiments of the disclosure.
FIG. 4B shows a DMR signal of primary liver cells in a biosensor liver cell culture system induced with 1 mM hydrogen peroxide 3 hrs after pretreatment of cells with rifampin at doses in the range of 625 nM to 40000 µM, in embodiments of the disclosure.
Figure 4:
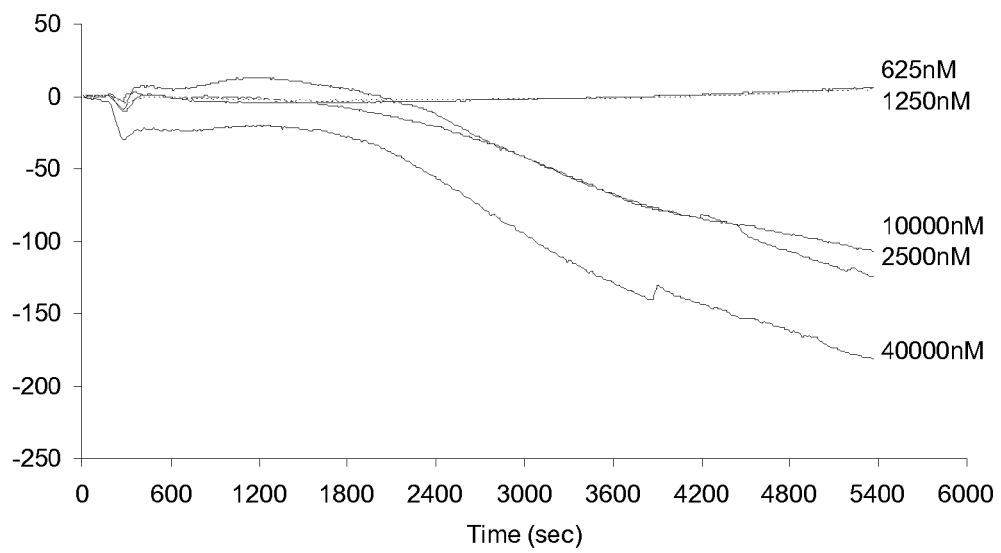

FIG. 4 summarizes the results obtained using the label-free biosensor cellular assays to probe the rifampin-induced toxicity in primary liver cells. FIG. 4A shows the real time kinetic DMR responses of primary liver cells cultured using the biosensor sandwich culture system upon exposure to rifampin at different doses, in the range of 625 nM up to 40000 nM. At all doses examined, rifampin did not result in any significant loss in local biomass density or cause any significant DMR signal.

Interestingly, after pretreatment of the primary liver cells with rifampin at different doses for a relatively short of period time (~1-4 hrs), the primary liver cells became susceptive to exposure to 1 mM $H_2O_2$, in a rifampin dose-dependent manner, as is shown in FIG. 4B.

Compared to those without any pretreatment in which 1 mM $H_2O_2$ did not cause any significant DMR signal (FIG. 3A), the primary liver cells responded to exposure with 1 mM $H_2O_2$ with a rifampin dose dependent N-DMR. As shown in FIGS. 4A and 4B, the higher the concentration of rifampin, the greater and faster the $H_2O_2$ induced N-DMR signal occurs. This indicates that rifampin at the high doses examined causes damage to primary liver cells possibly due to the increasing oxidization of lipid molecules, and that $H_2O_2$ can be used as a pharmacological probe to amplify the rifampin induced liver cell toxicity.

E. Example 4

Hydrogen Peroxide Also Amplifies the Toxicity of Acetaminophen Acting on Primary Liver Cells Cultured on the Biosensor Sandwich System Chemicals produce a wide variety of clinical and pathological hepatic injury. Biochemical markers (i.e. alanine transferase (ALT), alkaline phosphatase (ALP) and bilirubin) are often used to indicate liver damage. Liver injury is defined as rise in (a) ALT level more than three times of upper limit of normal (ULN), (b) ALP level more than twice ULN, or (c) total bilirubin level more than twice ULN if associated with increased ALT or ALP. Liver damage is further characterized into hepatocellular (predominantly initial Alanine transferase elevation) and cholestatic type (initial alkaline phosphatase rise). Many herbal, naturally occurring hepatotoxins, alternative remedies including Chinese herbal remedies such as Jin Bu Huan, and Ma-huan can also cause liver damage at high doses.

Acetaminophen (paracetamol, also known by the brand name Tylenol®), a non-steroidal anti-inflammatory drug (NSAID), has been widely used for over 50 years in the treatment of pain and fever and provides for the effective relief of these symptoms. It is safe when used at therapeutic doses. However, overdose (either intentional or accidental) can lead to serious and even fatal hepatotoxicity. Acetaminophen overdose is the most common cause of drug induced liver disease and acute liver failure worldwide. In the US, acetaminophen is responsible for up to 50% of all adult cases of acute liver failure.

An overdose of acetaminophen can cause severe liver injury, centrilobular-cell injury and even liver failure in experimental animals and humans. Toxicity requires formation of a reactive metabolite, presumably N-acetylbenzoquinone imine (NAPQI) or an intermediate resembling it, in excess of the available glutathione. After consumption of glutathione, NAPQI can covalently bind to a number of intracellular target proteins, which leads to a variety of cellular dysfunctions, including mitochondrial damage, ATP depletion, and mitochondrial oxidant stress. In recent years, an increasing number of authors have postulated that apoptosis plays a major role in AAP-induced liver failure. For the liver, it was hypothesized that 40% or more of the hepatocytes actually die by apoptosis. Apparent experimental evidence for apoptotic cell death after the overdose in vivo included DNA fragmentation and DNA laddering, cleavage of poly (ADP-ribose)polymerase, DNA strand breaks, and morphological evidence for apoptosis of individual hepatocytes.

In the liver, acetaminophen is metabolized to the non-toxic conjugated metabolites acetaminophen glucuronide and acetaminophen sulfate. These detoxification pathways account for over 90% of the acetaminophen metabolism by the liver. Under normal conditions, less than 10% of the acetaminophen is metabolized by the cytochrome P450 enzymes (primarily CYP 2E1, 1A2, and 3A4) to produce the toxic metabolic intermediate called N-acetyl-p-benzoquinoemine (NAPQI). The small amount of NAPQI formed is normally further detoxified by intracellular glutathione. In the cases of high drug load (such as intentional or accidental overdose), and/or low intracellular glutathione reserve (such as after fasting or alcohol use), NAPQI can covalently modify thiol groups on cellular proteins. The traditional thought is that such covalent protein adducts are the cause of liver cell or hepatocyte injury. However, it was demonstrated that the generation of NAPQI is necessary but not sufficient to account for acetaminophen-induced liver injury. The m-hydroxy isomer of acetaminophen, 3'-hydroxyacetanilide, is not hepatotoxic in mice, even though the amounts of covalent binding are almost equivalent. The covalent binding of 3'-hydroxyacetanilide is also located in the centrilobular hepatocytes, the area of the ensuing necrosis and covalent binding by the hepatotoxic isomer acetaminophen. These and other studies have raised the possibility that the amount of covalent binding is not a determinant of the final toxicity outcome.

Recently, genomic, metabonomic and proteomic approaches have been applied in the human hepatocyte chimeric mice model to investigate the mechanisms and pathways of acetaminophen induced toxicity. In this animal model, human hepatocytes were transplanted into transgenic mice. The replacement ratio of mouse liver with human liver in chimeric mice was estimated at 75-95%, with human specific metabolic responses to drugs observed. In acetaminophen-treated animals, perturbations in lipid metabolism, fatty acid transport, and glycolysis indicated suppression of the β-oxidation pathways of fatty acids, leading to the depletion of acetyl-CoA. Perturbations in the oxidative stress-related proteins such as peroxiredoxin 1 and catalase, were observed. These findings are in accordance with those observed in normal mice treated with acetaminophen. These data suggest that both intracellular mitochondrial and oxidative stress pathways were perturbed by the treatment of acetaminophen.

The question still remains as to whether it was the parent acetaminophen or the NAPQI metabolite responsible for the observed changes in mitochondrial energy status and oxidative stress. Data from the in vitro treatment of freshly-isolated mouse hepatocytes have provided mechanistic insight. In this in vitro model, acetaminophen-induced cell death occurs in two phases, a metabolic phase and an oxidative phase. The metabolic phase occurs with NAPQI formation, glutathione depletion and covalent protein binding. The oxidative phase occurs with increased oxidative stress, loss of mitochondrial membrane potential, mitochondrial permeability transition, and resulting toxicity. The oxidative phase does not require the presence of either acetaminophen or the NAPQI metabolite, as addition of acetaminophen in the second phase did not alter toxicity. This study raised the interesting possibility that while both acetaminophen and 3'-hydroxyacetanilide can initiate a similar metabolic phase, acetaminophen is unique in its ability to progress to the oxidative phase at least in the mouse hepatocytes. Further pathway studies using these two isomeric chemicals and the mouse hepatocyte model are required to delineate the differences in the triggering events leading the metabolic phase to oxidative phase. It was recently reported that delivery of nitric oxide (NO) in small amounts to the liver, via a novel derivative of the bile acid ursodeoxycholic acid, resulted in significant protection of the liver from acetaminophen-induced damage. NO appears to produce these beneficial actions through several mechanisms, including the suppression of synthesis of several proinflammatory cytokines. Therefore, acetaminophen is a classic example of a well-studied drug starting with the understanding of a single pathway (i.e., the metabolic activation by the cytochrome P450s), to multiple pathways involving a metabolic phase, an oxidative phase, several cytokines of the innate immune system, and stress kinases critical in the regulation of cytokine responses. Currently a collective body of in vitro and in vivo evidence suggests that multiple phases or steps of acetaminophen-induced liver injury are in line with the delayed on-set of liver injury biomarkers by acetaminophen treatment.

Figure 5:
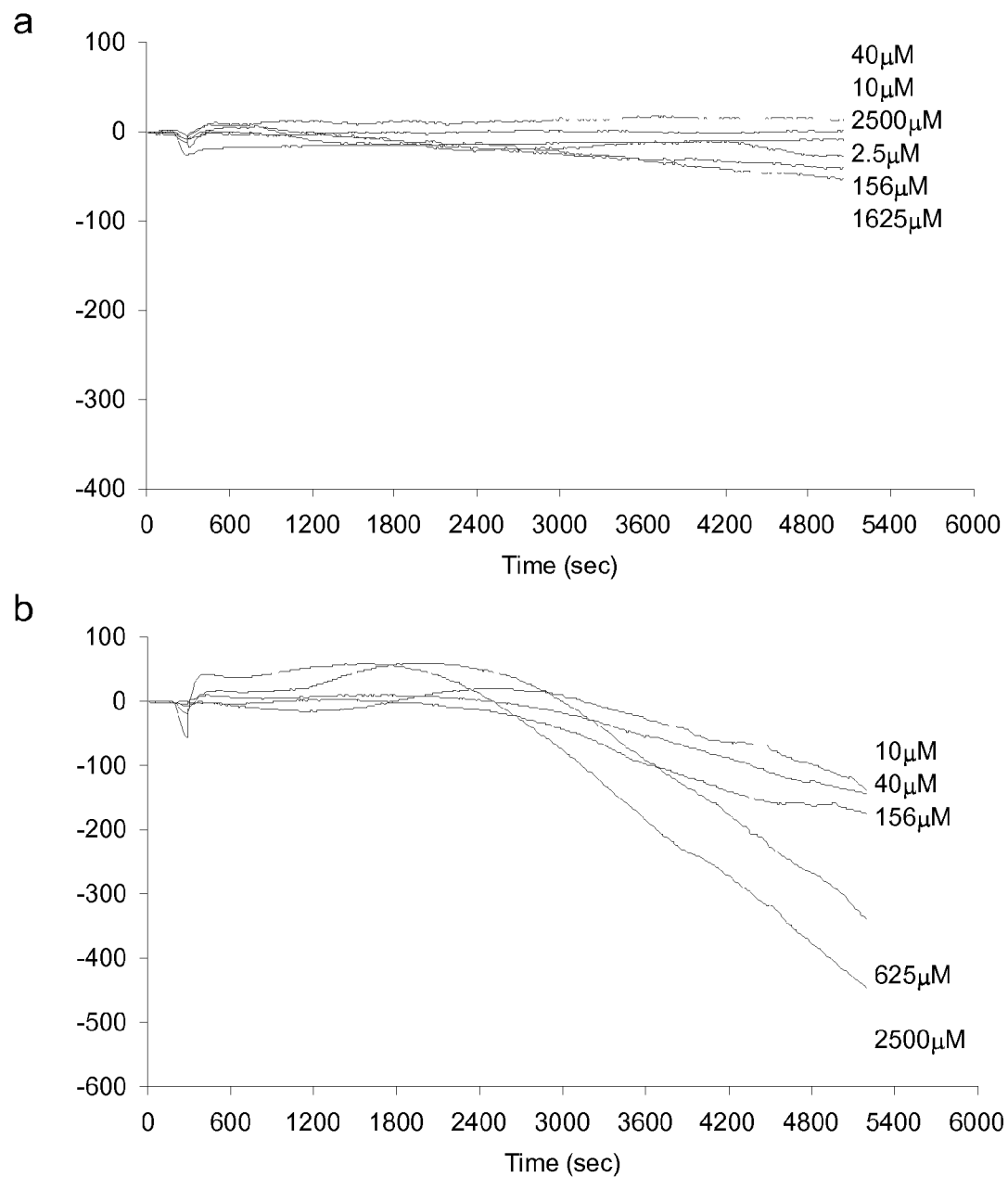
FIG. 5A shows a DMR signal of primary liver cells in a biosensor liver cell culture system induced with acetaminophen at doses in the range of 2.5 µM to 2500 µM, in embodiments of the disclosure.
FIG. 5B shows a DMR signal of primary liver cells in a biosensor liver cell culture system and (B) induced with 1 mM hydrogen peroxide 3 hrs after pretreatment of cells with acetaminophen at doses in the range of 10 µM to 2500 µM, in embodiments of the disclosure.

FIG. 5 summarizes the results obtained using the label-free biosensor cellular assays to probe the acetaminophen-induced toxicity in primary liver cells. FIG. 5A shows the real time kinetic DMR responses of primary liver cells cultured using the biosensor sandwich culture system upon exposure to acetaminophen at different doses, in the range of 2.5 µM up to 2.5 mM. At all doses examined, acetaminophen did not result in any significant DMR signal. This suggests that similar to rifampin, the acetaminophen-induced damage of liver cells, if any, cannot be directly detected by the biosensor cellular assays.

Interestingly, after pretreatment of the primary liver cells with acetaminophen at different doses for a relatively short of period time (~1-4 hrs), the primary liver cells became susceptive to exposure to 1 mM $H_2O_2$, strongly dependent on acetaminophen doses, as is shown in FIG. 5B. Compared to those without any pretreatment in which 1 mM $H_2O_2$ did not cause any significant DMR signal (FIG. 3A), the primary liver cells after treated with high doses of acetaminophen responded to exposure with 1 mM $H_2O_2$ with a N-DMR. The higher the concentration of acetaminophen, the greater the $H_2O_2$-induce-N-DMR signal, and the faster the onset time of the N-DMR. This indicates that acetaminophen at the high doses examined causes damage of the primary liver cells, and that $H_2O_2$ can be used as a pharmacological probe to amplify the acetaminophen induced liver cell toxicity.

F. Example 5

Hydrogen Peroxide Also Amplifies the Toxicity of SB203580 Acting on Primary Liver Cells Cultured on the Biosensor Sandwich System SB203580 and SB-202190 are potent p38MAPK inhibitors that can block interlukin-1 (IL-1) and tumour necrosis factor (TNF) production in human monocytes. To date, over 20 compounds have entered clinical trials with no small molecule inhibitors making it to the market. Most discontinued p38 inhibitors have failed due to safety concerns, most notably elevated liver enzymes and skin rash. Relatively little is known about the link between p38 and reported adverse events.

The p38 stress activated protein kinases are involved in regulating cell growth, cell differentiation, proliferation, apoptosis and response to inflammation and stress. The p38 family of protein kinases is regulated by multiple upstream kinases, MKK3, MKK6 and MKK4, in response to cellular stress, toll-like receptor ligands and IL-1, among others. There are four highly-related p38 isoforms (α, β, δ, and γ) with distinct tissue expression patterns. p38 α and β are expressed in most tissues including human lymphoid tissues, leukocytes, pancreas and liver, while γ and δ have a more limited distribution including skeletal muscle, heart lung, thymus and testis.

Elevated liver enzymes in human plasma have been reported for many p38 MAPK inhibitors. On-going research has demonstrated the role of p38 in a multitude of liver cell functions, including extracellular matrix production, growth regulation, cell volume regulation, ion and bile salt transport, gluconeogenesis and lipogenesis. Whether these functional roles of p38 are mechanistically linked to elevated liver enzymes in human plasma with p38 inhibitors is an open question.

Liver fibrosis is characterized by a deposition of extracellular matrix proteins as part of excessive wound healing in response to chronic stimuli. As part of this response, signaling from p38, and focal adhesion kinase-phosphatidylinositol 3-kinase-Akt-p70 S6 kinase (FAK-PI3K-Akt-S6K) cascades regulate the proliferation, cell cycle progression, as well as collagen gene expression in activated hepatic stellate cells. p38 signaling has been found to regulate 1 collagen gene expression by transcriptional activation and by increasing mRNA stability, thereby contributing to increased synthesis and deposition of type I collagen.

p38 has been demonstrated to play a role in growth regulation, mediating growth inhibitory effects in developing rat hepatocytes, as demonstrated via treatment with SB203580. PGC-1 and peroxisome proliferator—(PPAR) are downstream targets of p38. p38 phosphorylates the A/B domain of PPAR at Ser 6, 12 and/or 21. PPAR directly regulates genes that are involved implicated in the response to peroxisome proliferators, altering expression of cell cycle regulatory proteins, cell proliferation and apoptosis. Thus, survival signaling mediated by p38 via PPAR may provide a link between p38 inhibition and necrotic and/or apoptotic liver injury.

In addition to proliferative changes, liver regeneration and cholestasis are associated with adaptive changes in expression of gap and tight junctions. During hepatocyte regeneration following partial hepatectomy, dynamic changes in the formation of gap and tight junctions were, in part, regulated by p38 and independent of cell growth. Changes in expression and function of the gap junction protein, Cx32, and tight junction protein, claudin-1, were observed following SB203580 treatment.

Failure to regulate liver cell volume has been associated with liver cell injury resulting from alcohol, ischemia/reperfusion, and organ preservation. In hepatocytes, non-selective cation channels play a critical role in the maintenance of cell volume, many of which have been demonstrated to be under the influence of p38. Hypotonic exposure led to increased cell volume and increased p38 activity in a HTC rat hepatoma cell line. Constitutive p38 activity was demonstrated to be involved in sustaining the low Na+ permeability required for maintenance of cell volume. Na+ currents could be increased by inhibiting p38 activity with SB203580. In perfused rat liver, treatment with SB203580 has also been used to demonstrate the role of p38 in response to hypo-osmotic exposure via regulation of cell volume regulation. Swelling-induced activation of p38 is involved in volume regulatory K(+) efflux in liver. Further roles in regulating ion transport were elucidated with SB202190, demonstrating that liver plasma vesicles purified in the presence of SB202190 had lost the ability to accumulate Mg(2+) in exchange for intra-vesicular Na(+), following activation of protein kinase C signaling.

Complementing the role in ion transport, p38 also indirectly regulates bile salt transport. Trafficking of the bile salt export pump (BSEP) from the Golgi to the canalicular membrane has been shown to be regulated via p38 signaling in rat hepatocytes. Consequently, tauroursodesoxycholate (TUDC)-induced choleresis was demonstrated to be under the dual control of p38 and extracellular regulated kinase (ERK) regulation. SB202190 abolished the stimulatory effect of TUDC on taurocholate excretion in perfused rat liver.

Finally, p38 regulates both lipo- and gluconeogenic aspects of hepatocyte metabolism. Hepatic lipogenesis is the principal route for the conversion of excess carbohydrates into fatty acids and, upon dysregulation, leads to fatty liver. This process is coordinately regulated by insulin and glucagon, playing stimulatory and inhibitory roles, respectively. Following p38 inhibition, levels of plasma triglyceride and triglyceride accumulation in the liver were elevated in mice. Expression of essential lipogenic genes (SREBP-1, fatty acid synthase, hydroxyl-3-methylglutaryl coenzyme A reductase, farnesyl pyrophosphate synthase and cytochrome P-450-51) were increased following p38 inhibition in primary hepatocytes. p38 activation was shown to inhibit insulin-induced lipogenic genes. Insulin-induced expression of the PGC-1β gene, a key coactivator of SREBP-1c, was enhanced by p38 inhibition and suppressed by p38 activation.

Similarly, p38 has been identified as a critical signaling component in free fatty acid induced transcription of gluconeogenic genes. p38 activation was shown to be necessary for mid- and long-chain fatty acid induced transcription of PGC-1 and CREB, known gluconeogenic regulators. Inhibition of p38 suppressed gluconeogenesis in liver along with key gluconeogenic genes, including phosphoenolpyruvate carboxykinase and glucose-6-phosphatase. Furthermore, p38 inhibition prevented PGC-1 transcription and CREB phosphorylation.

Figure 6:
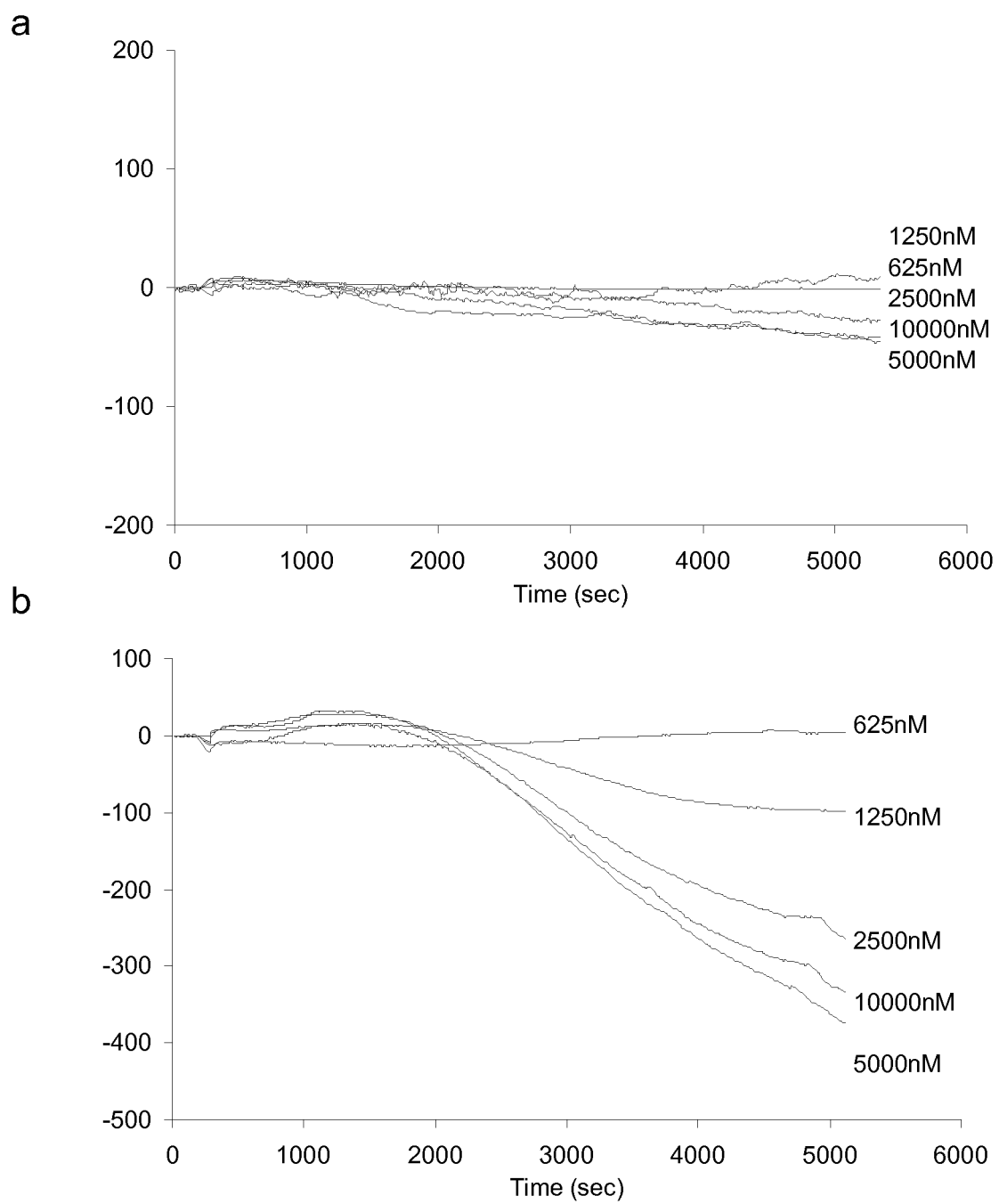
FIG. 6A shows a DMR signal of primary liver cells in a biosensor liver cell culture system induced with SB-203850 at doses in the range of 625 nM to 10000 µM, in embodiments of the disclosure.
FIG. 6B shows a DMR signal of primary liver cells in a biosensor liver cell culture system induced with 1 mM hydrogen peroxide 3 hrs after pretreatment with SB-203850 at doses in the range of 625 nM to 10000 nM, in embodiments of the disclosure.

FIG. 6 summarizes the results obtained using the label-free biosensor cellular assays to probe the SB203580-induced toxicity in primary liver cells. FIG. 6A shows the real time kinetic DMR responses of primary liver cells cultured using the biosensor sandwich culture system upon exposure to acetaminophen at different doses, in the range of 625 nanomolar up to 10000 nanomolar. At all doses examined, SB203580 did not result in any significant DMR signal. This suggests that similar to rifampin, the SB203580-induced damage of liver cells if any can not be directly detected by the biosensor cellular assays.

Interestingly, after pretreatment of the primary liver cells with SB203580 at different doses for a relatively short of period time (~1-4 hrs), the primary liver cells became susceptive to exposure to 1 mM $H_2O_2$, strongly dependent on SB203580 doses. Compared to those without any pretreatment in which 1 mM $H_2O_2$ did not cause any significant DIVER signal (FIG. 3a), the primary liver cells after treatment with high doses of SB203580 responded to 1 mM $H_2O_2$ exposure with a N-DMR. The higher the concentration of SB203580 is, the greater the $H_2O_2$-induced N-DMR signal is, the faster onset time of the N-DMR is. This indicates that SB203580 at the high doses examined causes damage of the primary liver cells, and that $H_2O_2$ can be used as a pharmacological probe to amplify the SB203580 induced liver cell toxicity.

Taken together, the three different classes of compounds, rifampin, acetaminophen, and SB203580, increase the susceptibility of primary liver cells cultured within the biosensor sandwich culture system to $H_2O_2$-induced apoptosis in a dose-dependent manner, suggesting a common mechanism of these compounds causing liver cell toxicity, which is possible due to the increased oxidization level of liver cells after being administrated with these toxic compounds. These studies also suggest that the present invention not only discloses methods to amplify any compound-induced cell toxicity, particularly liver cells, but also enables the study of cellular mechanisms of compound-induced liver cell toxicity.

G. Example 6

Screening Compounds or Identifying Targets that Alter the Susceptibility of Cells to Damage Induced by Hypoxia or Hydrogen Peroxide Exposure Hypoxia is a deficiency of oxygen in the body. Hypoxia is an important regulatory stimulus for diverse biological processes such as angiogenesis and thrombosis. The development of atherosclerotic plaques is associated with neovascularization in the plaque. For the neointimal angiogenesis, hypoxia of the vessel wall has been considered to be an important stimulus, because neovascularization develops in response to inadequate perfusion through the thickened intima. The molecular mechanisms which control hypoxia-induced gene expression have been extensively studied. Under low oxygen, a variety of cells produce many vasoactive substances such as plasminogen activator inhibitor-1 (PAI-1) and vascular endothelial growth factor (VEGF). Expression of these genes is regulated by hypoxia-inducible factor-1 (HIF-1), a transcription factor whose levels are tightly regulated by oxygen levels. Under normoxic conditions, HIF-1 is ubiquitinated and proteosomally degraded. Once oxygen concentration is decreased, HIF-1 escapes the ubiquitination/degradation. Its protein level becomes sufficient to translocate into the nucleus along with its heterodimer partner HIF-1β, and then it binds to a hypoxia-response element, thus activating hypoxia-sensitive genes.

Reactive oxygen species, such as hydrogen peroxide ($H_2O_2$) and superoxide anion ($O_2-\cdot$), have been implicated in diverse pathophysiological responses of the cardiovascular system, including induction of vascular smooth muscle cell (VSMC) proliferation, release/activation of paracrine factors and endothelial dysfunction. An in vivo study demonstrated ROS were produced in human atherosclerotic plaques.

Figure 7:
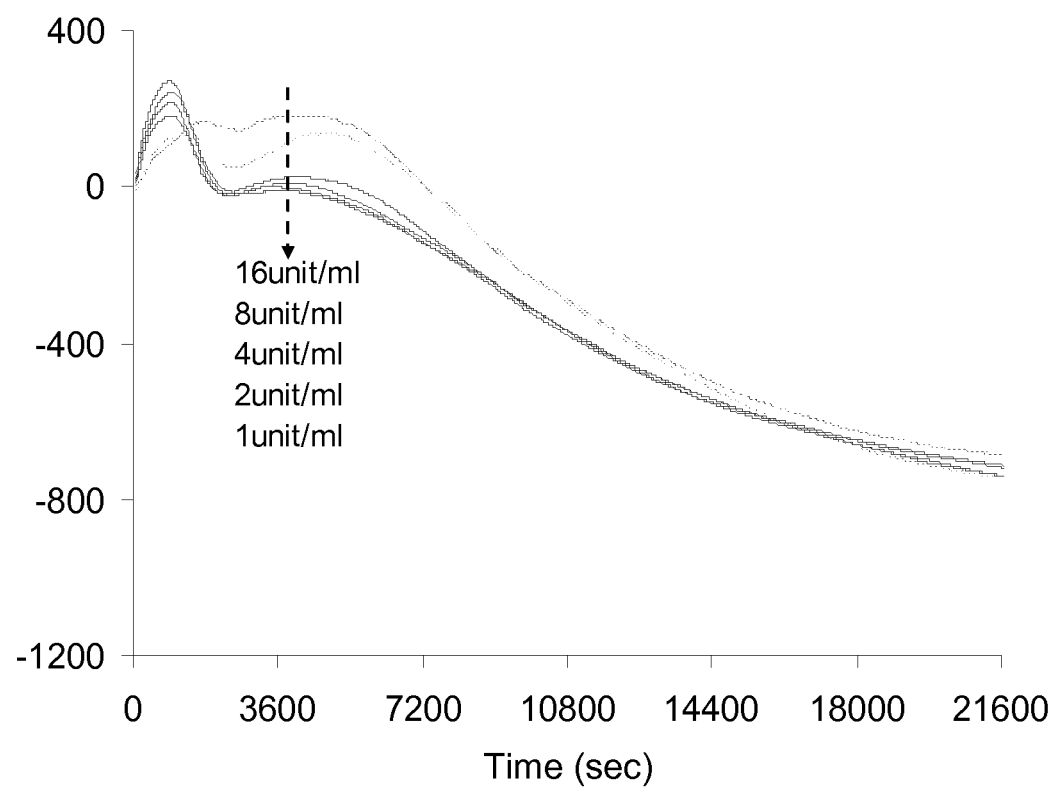
FIG. 7 shows a DMR signal of human cancer line A549 cells induced with 2 mM hydrogen peroxide 1 hr after pretreatment with thrombin at doses in the range of 1 unit/ml to 16 unit/ml. The kinetic responses were normalized at the time point 2 min before the addition of $H_2O_2$.

FIG. 7 shows the real time kinetics of human lung cancer cell line A549 upon exposure to 2 mM $H_2O_2$ with or without any pretreatment with thrombin. When the A549 was not pretreated with any thrombin, the cells responded with a complicated DMR signal, consisting of four phases: an initial increased signal P-DMR, followed by a rapid decaying signal (N-DMR), a slightly increased signal or plateau DMR lasting for about 1 hr, and a prolonged second N-DMR signal. The large amplitude of the second N-DMR signal indicates the significant loss of local biomass density within the detection zone of the biosensor, indicative of cell apoptosis which leads to the release of cellular matters from the bottom portion of cells cultured on the biosensor surface. However, as the concentration of thrombin increases, the initial rapid responses became partially suppressed, and the plateau phase became elevated. The onset time for the second N-DMR event is delayed by at least 15 min. These results suggest that thrombin is protective of $H_2O_2$-induced A549 apoptosis. Based on the amplitudes of the rapid P-DMR event, the potency of thrombin to alter such response was estimated to be ~4 unit/ml, corresponding to the $EC_{50}$ to activate endogenous protease activated receptor subtype 1 (PAR1) (data not shown), suggesting that the activation of PAR1 plays an important role of thrombin effect on the $H_2O_2$-induced A549 apoptosis.

In contrast, the activation of endogenous beta2-adrenergic receptor in A431 cells potentiated the $H_2O_2$-induced apoptosis of A431 cells cultured on the biosensor surface (data not shown). These results suggest that the present invention also enables screening compounds that can be protective or potentiate the $H_2O_2$-induced cell apoptosis, or identifying targets whose activation can be protective or potentiate the $H_2O_2$-induced cell apoptosis.

The invention claimed is:

1. A label-free method for indirectly characterizing the toxicity of a molecule to liver cells, the method comprising:
   a. providing a label-free biosensor comprising a substrate, a transducer in or on the substrate and liver cells immobilized on the surface of the substrate of the biosensor, wherein the immobilized liver cells are immobilized between nanoscale or microscale clusters of a first extracellular matrix material coated on the surface of the substrate of the biosensor and an overlay of a second extracellular matrix material;
   b. contacting the immobilized liver cells with a molecule;
   c. contacting the molecule-treated immobilized liver cells with an amplifying marker; and
   d. detecting and comparing the amplifying marker induced biosensor response of the liver cells in the presence and absence of the molecule.

2. The method of claim 1, wherein the first and second extracellular matrix materials comprise at least one of: collagen I, collagen IV, laminin, gelatin, polysaccharide, fibronectin, Matrigel, or a combination thereof.

3. The method of claim 1, wherein the immobilized liver cells retain at least a portion of their metabolic functions.

4. The method of claim 1, wherein the liver cells comprise at least one of: a primary liver cell, a transformed liver cell, an immortalized liver cell, or a combination thereof.

5. The method of claim 4, wherein the liver cells further comprise a helper cell selected from a hepatic stellate cell or a Kupffer cell.

6. The method of claim 1, wherein the amplifying marker comprises at least one of: hydrogen peroxide, ethanol, a hepatotoxin, carbonyl cyanide m-chlorophenyl hydrazone, dimethyl sulfoxide, or a combination thereof.

7. The method of claim 1, wherein the amplifying marker comprises hydrogen peroxide.

8. The method of claim 1, wherein the detected biosensor response comprises the dynamic mass redistribution of the liver cells.

9. The method of claim 1, further comprising detecting and comparing the molecule induced biosensor response of the liver cells in the presence and absence of a hepatotoxin.

10. The method of claim 1, wherein the amplifying marker amplifies toxicity of the molecule to liver cells.

11. The method of claim 1, wherein the amplifying marker amplifies protectiveness of the molecule to the liver cells.

12. The method of claim 1, wherein the liver cells become more susceptible to the amplifying marker as a result of exposure to the molecule.

13. The method of claim 1, wherein the liver cells become more resistant to the amplifying marker as a result of exposure to the molecule.

14. The method of claim 1, wherein the transducer is an optical transducer, an electrical transducer, a calorimetric transducer, an acoustic transducer, or a magnetic transducer.

15. The method of claim 1, wherein the biosensor is an optical biosensor, wherein the optical biosensor measures changes in local refractive index at or near the biosensor surface.

16. A label-free method for indirectly characterizing the toxicity of a molecule to liver cells, the method comprising:
   a. providing a label-free biosensor comprising a substrate, a transducer in or on the substrate and liver cells immobilized on the surface of the substrate of the biosensor, wherein the immobilized liver cells are immobilized between nanoscale or microscale clusters of a first extracellular matrix material coated on the surface of the substrate of the biosensor and an overlay of a second extracellular matrix material thereby forming a monolayer sandwiched between the first and second extracellular materials, and wherein the immobilized liver cells retain at least a portion of their metabolic functions;
   b. contacting the immobilized liver cells with a molecule;
   c. contacting the molecule-treated immobilized liver cells with an amplifying marker; and
   d. detecting and comparing the amplifying marker induced biosensor response of the liver cells in the presence and absence of the molecule.

17. A label-free method for indirectly characterizing the toxicity of a molecule to liver cells, the method comprising:
   a. providing a label-free biosensor comprising a substrate, a transducer in or on the substrate and liver cells immobilized on the surface of the substrate of the biosensor, wherein the immobilized liver cells are immobilized between nanoscale or microscale clusters of a first extracellular matrix material coated on the surface of the substrate of the biosensor and an overlay of a second extracellular matrix material;
   b. contacting the immobilized liver cells with a molecule;
   c. contacting the molecule-treated immobilized liver cells with an amplifying marker; and
   d. detecting and comparing the amplifying marker induced biosensor response of the liver cells in the presence and absence of the molecule;
   wherein the first extracellular matrix material comprises collagen I and the second extracellular matrix material comprises Matrigel.

* * * * *